(12) United States Patent
Robar et al.

(10) Patent No.: US 8,712,011 B2
(45) Date of Patent: Apr. 29, 2014

(54) METHODS AND APPARATUS FOR IMAGING IN CONJUNCTION WITH RADIOTHERAPY

(71) Applicant: Dalhousie University, Halifax (CA)

(72) Inventors: James Leonard Robar, Halifax (CA); Alexander Owen MacDonald, Halifax (CA)

(73) Assignee: Dalhousie University, Halifax, CA (US)

( * ) Notice: Subject to any disclaimer, the term of this patent is extended or adjusted under 35 U.S.C. 154(b) by 0 days.

(21) Appl. No.: 14/038,707

(22) Filed: Sep. 26, 2013

(65) Prior Publication Data

US 2014/0031603 A1 Jan. 30, 2014

Related U.S. Application Data

(63) Continuation of application No. 13/042,162, filed on Mar. 7, 2011, now Pat. No. 8,565,377.

(51) Int. Cl.
*A61N 5/10* (2006.01)

(52) U.S. Cl.
USPC .............................................. 378/65; 378/62

(58) Field of Classification Search
USPC .................. 378/62, 65, 108, 145, 147–153
See application file for complete search history.

(56) References Cited

U.S. PATENT DOCUMENTS

| | | |
|---|---|---|
| 6,618,467 B1 | 9/2003 | Ruchala et al. |
| 6,915,005 B1 | 7/2005 | Ruchala et al. |
| 7,046,831 B2 | 5/2006 | Ruchala et al. |
| 7,221,733 B1 | 5/2007 | Takai et al. |
| 7,289,599 B2 | 10/2007 | Seppi et al. |
| 2009/0225932 A1 | 9/2009 | Zhu et al. |
| 2010/0119033 A1 | 5/2010 | Li et al. |
| 2010/0246752 A1 | 9/2010 | Heuscher et al. |
| 2012/0008744 A1 | 1/2012 | Bani-Hashemi |

FOREIGN PATENT DOCUMENTS

WO 0059576 A1 10/2000

OTHER PUBLICATIONS

Robar, J. L. et al., "Megavoltage planar and cone-beam imaging with low-Z targets: Dependence of image quality improvement on beam energy and patient separation", Med. Phys. 36(9), Sep. 2009.
Zou, Y. et al., "Exact image reconstruction on P1-lines from minimum data in helical cone-beam CT", Phys. Med. Biol. 49(6), Mar. 21, 2004.
Murphy, M. J. et al., "The management of imaging dose during image-guided radiotherapy: Report of the AAPM Task Group 75", Med. Phys. 34(10), Oct. 2007.
Vassiliev, O. N. et al. "Treatment-Planning Study of Prostate Cancer Intensity-Modulated Radiotherapy with a Varian Clinac Operated Without a Flattening Filter", I.J. Radiation Oncology 68(5), 2007.

(Continued)

*Primary Examiner* — Courtney Thomas
(74) *Attorney, Agent, or Firm* — Oyen Wiggs Green & Mutala LLP

(57) ABSTRACT

Methods and apparatus for planning imaging include planning imaging in conjunction with planning a radiation treatment. A radiation dose due to planned imaging may be calculated and used in optimizing a plan for delivering therapeutic radiation. Imaging and treatment may be performed using radiation beams having different characteristics. In some embodiments an imaging beam is generated using a low-Z target and a therapy beam is generated using a high-Z target. A radiation treatment planning system may include data characterizing both the imaging beam and the treatment beam.

36 Claims, 17 Drawing Sheets

(56) References Cited

OTHER PUBLICATIONS

Sillanpaa, J. et al., "Developments in megavoltage cone beam CT with an amorphous silicon EPID: Reduction of exposure and synchronization with respiratory gating", Med. Phys. 32(3), Mar. 2005.

Kadrmas, D. J. et al., "Truncation artifact reduction in transmission CT for improved SPECT attenuation compensation", Phys. Med. Biol. 40, 1995.

Ford, E. C. et al., "Cone-beam CT with megavoltage beams and an amorphous silicon electronic portal imaging device: Potential for verification of radiotherapy of lung cancer", Med. Phys. 29 (12), Dec. 2002.

Cho, S. et al., "Region-of-interest image reconstruction in circular cone-beam microCT", Med. Phys. 34(12), Dec. 2007.

Chen, L. et al., "Feasibility of volume-of-interest (VOI) scanning technique in cone beam breast CT—a preliminary study", Med. Phys. 35(8), Aug. 2008.

Roberts, D.A. et al., "Comparative study of a low-Z cone-beam computed tomography system", Phys. Med. Biol. 56 (14):4453-4464, Jun. 30, 2011.

Fast, M.F. et al., "Performance characteristics of a novel megavoltage cone-beam-computed tomography device", Phys. Med. Biol. 57(3):N15-N24, Jan. 18, 2012.

METHODS AND APPARATUS FOR IMAGING IN CONJUNCTION WITH RADIOTHERAPY

CROSS-REFERENCE TO RELATED APPLICATIONS

This application is a continuation of U.S. patent application Ser. No. 13/042,162 filed 7 Mar. 2011 and entitled METHODS AND APPARATUS FOR IMAGING IN CONJUNCTION WITH RADIOTHERAPY which is hereby incorporated herein by reference for all purposes.

TECHNICAL FIELD

The invention relates to medical imaging and to radiotherapy. Embodiments provide imaging methods that may be performed using MeV radiation sources.

BACKGROUND

Cancer is a disease characterized by the rapid uncontrolled growth of cells that are able to invade nearby tissues, as well as metastasize to other areas of the body. Several methods for cancer treatment are employed today. These include systemic treatments such as chemotherapy, hormone therapy or biological therapy, and local treatments such as surgery, cryosurgery, or radiotherapy.

Radiotherapy is an important treatment for many types of cancer. Recent advances in radiotherapy have provided finer control over the distribution of radiation dose delivered to subjects' tissues. This fine control can be exploited to permit radiation to be delivered to a lesion such as a tumor while sparing normal tissue that is closely adjacent to the tumor. Imaging is an important adjunct to radiotherapy. Imaging is used to identify the extent of lesions that may be treated by radiotherapy as well as to determine the location of the lesion relative to other nearby anatomical structures. Imaging is also used to monitor the response of a subject to treatment.

The use of radiotherapy is not limited to cancer treatment. Radiotherapy can also be useful in the treatment of other conditions.

Image-guided radiation therapy (IGRT) is a technique that involves acquiring images during a course of radiation therapy. IGRT can deliver radiation with improved accuracy by taking into account changes in the subject as revealed by the images. Images may be taken before or during the delivery of radiation. Some radiation sources, such as linear accelerators are equipped with imaging systems such as kV X-ray imagers for acquiring images of a subject while the subject is positioned for the delivery of radiation.

SUMMARY OF THE INVENTION

The invention has a number of aspects. Some of these aspects relate to features that can be applied individually or in combination with other aspects. A non-limiting list of aspects of the invention includes: treatment planning systems for planning radiotherapy treatments that include functionality for planning imaging sequences; methods for planning radiotherapy treatments that take into account imaging dose; methods for acquiring images in the course of radiotherapy treatments; radiotherapy treatment systems that incorporate imaging functionality; and media containing computer instructions for causing a processor to perform methods as described herein.

One aspect provides methods for imaging comprising generating a cone X-ray beam by directing a megavolt electron beam at a low-atomic-number target, shaping the cone X-ray beam to match a shape of a volume of interest (VOI) in a subject, and detecting X-rays of the cone X-ray beam that have passed through the subject at an imaging X-ray detector. The method may be practised using a medical linear accelerator to generate the electron beam. In some embodiments, shaping the cone X-ray beam comprises adjusting positions of leaves of a multi-leaf collimator and/or rotating a multi-leaf collimator about its axis.

In some embodiments the low-atomic-number target is supported on a gantry that is rotatable relative to the subject and the method comprises repeating: shaping the cone X-ray beam to match a shape of a volume of interest in a subject; and detecting at the imaging X-ray detector X-rays of the cone X-ray beam that have passed through the subject to obtain a plurality of images for a corresponding plurality of different angles of the gantry relative to the subject.

Another aspect provides a method for planning a radiation treatment for delivery by a radiotherapy apparatus comprising a radiation source that is rotatable to different beam angles around a subject and a beam shaper configured to control a shape of a radiation beam emitted by the radiation source. The method comprises defining at least one set of imaging conditions. Each set of imaging conditions comprises at least a beam angle and a beam shape for exposing at least one volume of interest to radiation. The method estimates a volumetric radiation dose for the at least one set of imaging conditions and establishes a plan for a therapeutic radiation treatment. The plan comprises apertures for a plurality of beam angles. Establishing the plan comprises optimizing the apertures to deliver a desired radiation dose to a target region of a subject while maintaining radiation dose to tissues outside of the target region below one or more thresholds. Establishing the plan comprises taking into account the estimated volumetric radiation dose for the at least one set of imaging conditions at least in a selected region outside of the target region.

In some embodiments, optimizing the apertures comprises estimating volumetric radiation doses for the apertures and summing the volumetric radiation doses for the apertures together with the estimated volumetric radiation dose for the at least one set of imaging conditions.

In some embodiments the selected region outside of the target region corresponds to a sensitive tissue desired to be spared by the radiation treatment and the optimization comprises applying a cost function that values minimizing dose to the selected region.

Another aspect provides a method for planning a radiation treatment. The method comprises: planning exposures of a subject to radiation to be used for imaging; computing a contribution to dose from the imaging exposures; and using the imaging dose contributions in generating a treatment plan. The method may be performed automatically by a computerized treatment planning system. The treatment plan may comprise control signals that may be applied to control a radiation delivery system.

Another aspect provides an imaging method comprising, for each of a plurality of different beam angles, controlling a beam shaper to shape a radiation beam such that delivery of radiation is primarily limited to paths that pass through a plurality of volumes of interest within a subject; obtaining images of radiation that has passed through the volumes of interest; and, processing the images to obtain volumetric images of the plurality of volumes of interest.

Further aspects of the invention and features of specific example embodiments of the invention are described below.

BRIEF DESCRIPTION OF THE DRAWINGS

The accompanying drawings illustrate non-limiting embodiments of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Figure 1:
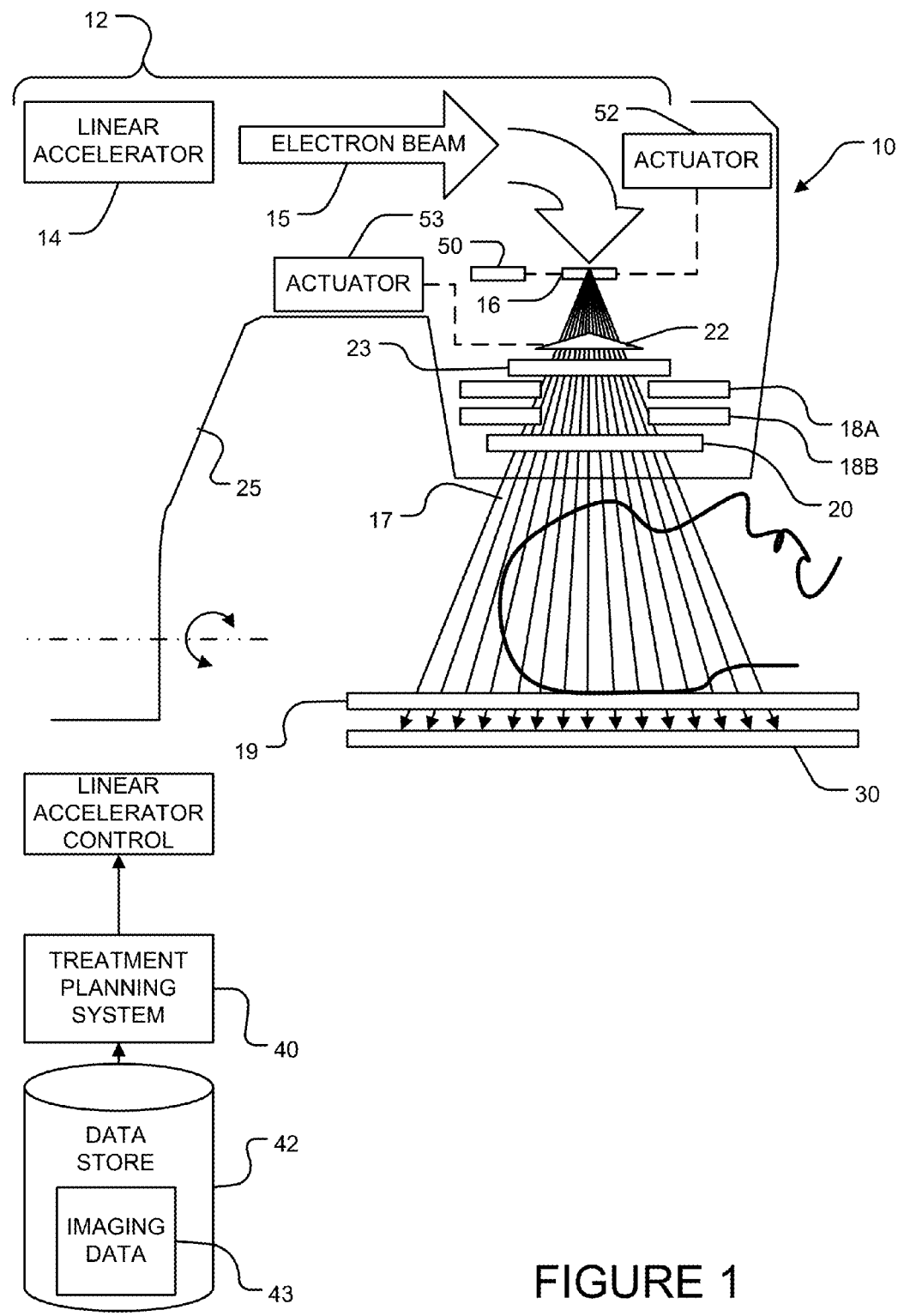
FIG. 1 is a block diagram of radiotherapy apparatus according to an example embodiment.

FIG. 1 is a block diagram of radiotherapy apparatus 10. Radiotherapy apparatus 10 comprises a source 12 of radiation. In the illustrated embodiment, source 12 comprises a linear accelerator 14 that accelerates a beam 15 of electrons to MeV energies and directs the electron beam 15 at a target 16 of a high atomic number (high Z) material. Target 16 may, for example, comprise tungsten or tungsten backed with copper. Suitable targets for generating X-rays suitable for radiotherapy in a linear accelerator are commercially available. Electron beam 15 interacts with target 16 to generate a beam 17 of X-rays.

X-ray beam 17 is shaped by upper and lower sets of jaws 18A and 18B and a multileaf collimator 20 before being delivered toward a patient support 19 on which a subject may be supported for treatment. Apparatus 10 additionally includes a flattening filter 22 that increases the uniformity of the fluence of X-ray beam 17 and an ionization chamber 23 that can be applied to measure the fluence of X-ray beam 17.

Apparatus 10 comprises a gantry 25 that permits an angle θ at which X-ray beam 17 is incident toward patient support 19 to be rotated. In some cases, gantry 25 permits rotation through a full 360 degrees around patient support 19.

An imaging detector 30 is opposed to target 16 such that some X-rays in beam 17 originating at target 16 can pass through a subject on patient support 19 and be detected by imaging detector 30. Imaging detector 30 may comprise, for example, an electronic portal imaging device.

Imaging detector 30 may comprise an amorphous silicon flat panel detector. Such detectors are in widespread use for detecting MV photons in medical linear accelerators. Such detectors typically comprise a layer of copper overlying the active detector matrix. The copper layer increases detection efficiency for MV photons. Where imaging is performed with lower energy photons, as described below, it is advantageous (but not required) that imaging detector 30 not have such a copper layer.

A treatment planning system 40 generates control parameters for apparatus 10. The control parameters may, for example, specify a number of units of radiation to be delivered to a subject for each of some number of corresponding gantry angles, MLC rotation angles and MLC leaf settings. The control parameters may specify conditions for a number of discrete radiation exposures (a step-and-shoot mode) and/or conditions for dynamic delivery of radiation (e.g. delivery of radiation while a configuration of apparatus 10 is changing). Apparatus 10 may be controlled according to the control parameters generated by treatment system 40 to deliver radiation to a subject according to a treatment plan.

Treatment planning system 40 may comprise a computer system executing software that generates a treatment plan under the supervision of and/or with the assistance of a human operator. Treatment planning system 40 has access to a set of image data for a subject. The image data may, for example, comprise 3D data such as results of a computed tomography (CT) scan. In the illustrated embodiment, treatment planning system 40 has access to a data store 42 containing imaging data 43 for a subject.

One example of a treatment planning system is the ECLIPSE™ treatment planning system available from Varian Medical Systems of Palo Alto Calif.

Contrast to noise ratio (CNR) is a useful indicator of image quality. One way to define CNR is as follows:

$$CNR = \frac{|\bar{S}_m - \bar{S}_b|}{\sigma_b} \quad (1)$$

where: $\bar{S}_m$ is the average signal in the subject being imaged; $\bar{S}_b$ is the average signal in the background and $\sigma_b$ is the standard deviation of the signal in the background.

CNR can be increased by increasing dose because, in general, the available means for increasing dose (e.g. increasing the number of exposures by taking images from more angles, increasing the X-ray fluence rate, or increasing slice size) can all result in reductions in quantum noise. However, it is generally considered desirable to keep imaging doses as small as practical.

It has been determined that when X-rays resulting from the interaction of electron beam 15 with low-Z target 50 are used for imaging, the resulting images can have significantly higher contrast to noise ratio (CNR) than images based on X-rays resulting from the interaction of electron beam 15 with high-Z target 16.

To facilitate improved imaging, apparatus 10 includes a second target 50. Second target 50 comprises a low-atomic-number (Low Z) material. For example, second target 50 may comprise aluminum (atomic number 13) or beryllium (atomic number 4) or another suitable element having an atomic number in the range of 6 to 13, for example. In some embodiments second target 50 comprises an element having an atomic number in the range of 8 to 20. Second target 50 is preferably sufficiently thick that electron beam 15 does not pass through second target 50 significantly. In some embodiments, second target 50 has a thickness of 5 mm or more or 3 mm or more. However, in some embodiments, especially those in which the energy of electron beam 15 is reduced, second target 50 may be thinner and still stop essentially all electrons of electron beam 15. It is typically advantageous to make second target 50 no thicker than necessary to provide appropriate mechanical strength and stop electron beam 15.

In the illustrated embodiment, apparatus 10 comprises an actuator 52 configured to insert low-Z target into electron beam 15 while removing high-Z target 16 from the path of electron beam 15 or vice versa. There are a number of ways in which switching among targets 16 and 50 may be accomplished. These include, for example, steering electron beam 15 to one or the other of targets 16 and 50; rotating or translating a carousel or other carrier on which targets 16 and 50 are supported; providing separate mechanisms for moving targets 16 and 50 into and out of the path of electron beam 15 and controlling those mechanisms in a coordinated manner; manually operating a mechanism to remove target 16 and replace it with target 50; etc.

A beneficial feature arising from the use of a low-Z target 50 for generating an imaging beam is that, for a given electron beam current, X-ray photon generation is less efficient that for higher-Z targets. For typical electron currents produced by a medical linear accelerator, precise control of radiation dose can be maintained even at low exposures.

It has also been determined that CNR may be further improved by imaging without a flattening filter 22. The illustrated apparatus 10 comprises an actuator 53 for moving flattening filter 22 into or out of the path of X-ray beam 17. In some embodiments actuators 52 and 53 are combined or operated in a coordinated fashion to provide an imaging configuration—in which electron beam 15 impinges on low-Z target 50 and flattening filter 22 is not present, and a radiotherapy configuration—in which electron beam 15 impinges on high-Z target 16 and flattening filter 22 is present in the path of X-ray beam 17.

Some linear accelerators provide carousels intended for holding flattening filters. The carousels are rotatable to bring a desired flattening filter into the beam. Some embodiments exploit the carousel to hold low-Z target 50 in place of a flattening filter. In such embodiments the linear accelerator may be placed into an imaging mode by removing high-Z target 16 from electron beam 15, rotating the carousel to bring low-Z target 50 into the path of the electron beam and setting parameters of the electron beam (e.g. beam current and beam energy) to yield an X-ray beam 17 having properties that are better for imaging (e.g. providing better contrast) than the X-ray beam 17 resulting from impingement of the MeV electron beam 15 on high-Z target 16.

The quality of X-ray beam 17 can be further improved by reducing the energy of electron beam 15. For example, some medical linear accelerators can produce electron beams with energies of 1.75 MeV or lower. With current linear accelerator designs the electron current (and consequently the X-ray beam flux) falls with decreasing electron energy. This can place a lower limit on the electron beam energy that it is practical to use. In some embodiments, the control of a linear accelerator is set to produce a lower energy electron beam 15 when switching to a low-Z target 50 and to increase the energy of electron beam 15 when switching back to high-Z target 16. In some embodiments the electron beam energy is set to a value of 3 MeV or less for generating an imaging X-ray beam 17.

Figure 2:
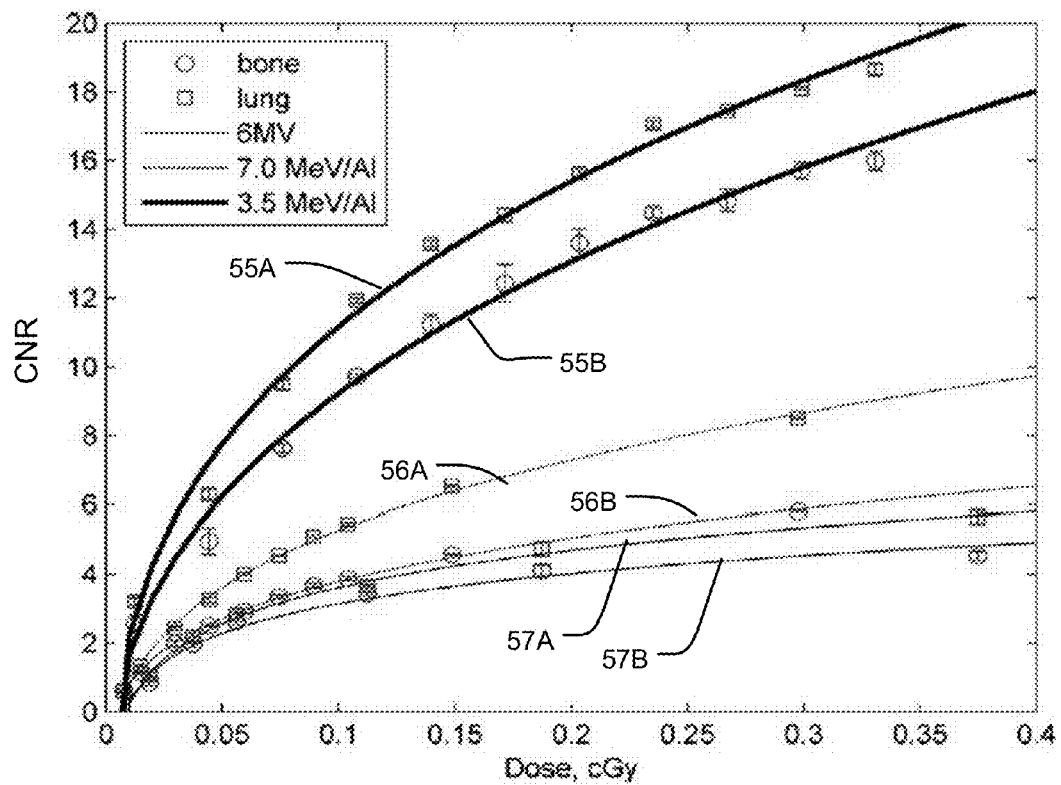
FIG. 2 is a graph illustrating CNR as a function of dose for bone and lung tissue images for three different X-ray beams.

FIG. 2 is a graph illustrating CNR as a function of dose for bone and lung tissue images for three different X-ray beams. Curves 55A and 55B are for a beam generated by impinging a 3.5 MeV electron beam on an aluminum target. Curves 57A and 57B are for a 6 MV therapeutic radiation beam. Curves 56A and 56B are for a beam generated by impinging a 7.0 MeV electron beam on an aluminum target. It can be seen from FIG. 2 that, for the same CNR, using the 3.5 MeV electron beam with a low-Z target can reduce dose by a factor exceeding 7 as compared to images made using the 6 MV therapeutic beam. FIG. 2 is taken from Robar et al., *Megavoltage cone-beam imaging with low-Z targets* Medical Physics, Vol. 36, No. 9, September 2009, which is hereby incorporated herein by reference.

In some embodiments cone beam imaging is performed using an X-ray beam derived from a MeV electron beam in which the beam is shaped to conform to the beam's-eye-view profile of a volume of interest. The shape of the beam may be controlled by a multileaf collimator on its own or in combination with adjustable jaws, for example. In some embodiments the X-ray beam is generated using a low-Z target such as an aluminum carbon or beryllium target. In some embodiments a flattening filter is not present during the imaging.

The techniques for imaging volumes of interest described herein are not limited to X-ray beams generated by MV electron beams. These techniques may also be applied to kV on-board-imaging (OBI) systems of the type that are becoming common on medical linear accelerators. To apply these techniques using an OBI system one would need to equip the OBI system (kV x-ray source) with some type of beam shaping device such as a multileaf collimator.

In some embodiments planning for imaging is performed using a treatment planning system. Treatment planning systems typically include functions for setting a beam shaper to match projected contours of a target volume. Such functions may be applied in planning for imaging. The volume of interest may be selected to provide imaging information that is useful for guiding the delivery of radiotherapy. For example: the volume of interest may be selected to include all or a portion of a lesion to be treated as well as all or a portion of a sensitive structure nearby the lesion that it is intended to spare. As another example, the volume of interest may be selected to include a fiduciary marker (e.g. a feature of a bone or other object that can be used as a reference point for determining a position or orientation of a subject).

In some embodiments a treatment system includes data defining a three-dimensional shape of a lesion to be treated and data defining a volume of interest for imaging is created by expanding the three dimensional shape such that the imaging volume of interest includes the lesion as well as a layer of tissues immediately outside of the lesion. Radiation may be delivered in sessions over the course of several days. Some treatments may be spread out over weeks. Over such a period a subject may lose weight or gain or lose fluids. A lesion being treated may shrink or grow. Imaging of the volume of interest may be performed before each session, for example.

Obtaining images during the course of a radiation treatment can be especially beneficial in the case where a lesion being treated is in soft tissue and may move around depending upon the subject's posture or changes in the subject or cases where a lesion may change in shape or position during the time span over which the treatment is delivered.

As one example application, consider the case where a tumor or other lesion to be treated by radio therapy is close to a subject's spinal cord. It is desired to spare the spinal cord while delivering radiation to the lesion. An imaging volume of interest may include all or a portion of the lesion as well as all or a portion of the part of the spinal cord that passes near to the lesion. Images of this volume of interest may be co-registered with an image of a volumetric dose distribution to be delivered by a treatment plan and used to verify that a plan to deliver radiation to the lesion will, catch the entire lesion while, as much as possible sparing the spinal cord. One can determine from the image whether the subject's position is exactly correct such that the therapeutic radiation will be delivered to the lesion and avoid the spinal cord.

If the image indicates that the volumetric dose distribution to be delivered by the treatment plan is not ideal for some other reason—for example where the image indicates that: the lesion has grown so that a portion of the lesion would not be adequately irradiated by executing the treatment plan; or the lesion has shrunk so that areas external to the lesion would receive more radiation than necessary by executing the treatment plan—then it may be necessary to establish a new treatment plan based on new imaging.

The image can also be used to verify that the subject is positioned in such a manner that the planned radiation dose will be delivered to the tumor. As another example application a small volume of interest may include the prostate, as well as interfaces with the rectum and bladder. Shaping an X-ray cone beam to conform to such a volume of interest permits imaging the prostate while largely sparing peripheral volumes of the pelvis from radiation exposure.

An advantage of imaging using a shaped beam is that the total dose delivered during imaging is reduced since radiation dose is greatly reduced outside of the boundary of the shaped beam. However, image truncation resulting from the beam shaping can result in severe imaging artifacts that can deleteriously affect the usefulness of the resulting images. Such artifacts tend to arise particularly where a number of images are acquired and combined into a 3D dataset using computed tomography (CT) imaging techniques.

Some embodiments perform CT imaging using a cone beam. In such embodiments, images are obtained for each of a plurality of different gantry angles. For each of the images the cone beam is shaped to conform with the projection of a volume of interest. The shaping is performed taking into account the geometry of the cone beam. The projection is a conical projection following rays of the imaging cone beam. Since the beam is diverging the shape imposed by a beam shaper such as a multileaf collimator is magnified as the beam propagates to the subject. Consequences of this geometry are that beam shaper apertures set in a planning system to shape the beam to match a volume of interest need to be scaled to take into account this magnification.

Where an imaging beam has a different beam geometry from a therapeutic beam then this different beam geometry needs to be taken into account both for establishing beam shaper settings to appropriately shape the imaging beam and for scaling acquired images to provide accurate spatial calibration.

The resulting images are then combined to provide a 3D data set. In some such embodiments the individual images are filled outside of the projection of the volume of interest with image data. The image data used for the fill may be obtained in various ways from various sources as discussed below. Filling the individual images prior to combining them to yield a 3D dataset can significantly reduce truncation artifacts.

The filled images may be combined using suitable cone-beam CT (CBCT) techniques. CBCT imaging techniques which combine 2D images from multiple angles to provide a 3D dataset are known to those of skill in the art. In some embodiments, a Feldkamp-Kress-Davis (FDK) filtered back-projection algorithm is applied for reconstructing images from the dataset. Optionally the images are filtered prior to back-projection. For example, Shepp-Logan, Hamming, Cosine or Hann filters may be applied. Cone-beam CT imaging software for processing sets of images into 3D datasets and reconstructing images from the datasets is commercially available. Such software may be applied to combine the filled individual images and to generate reconstructed images of the subject in desired planes.

Figure 3:
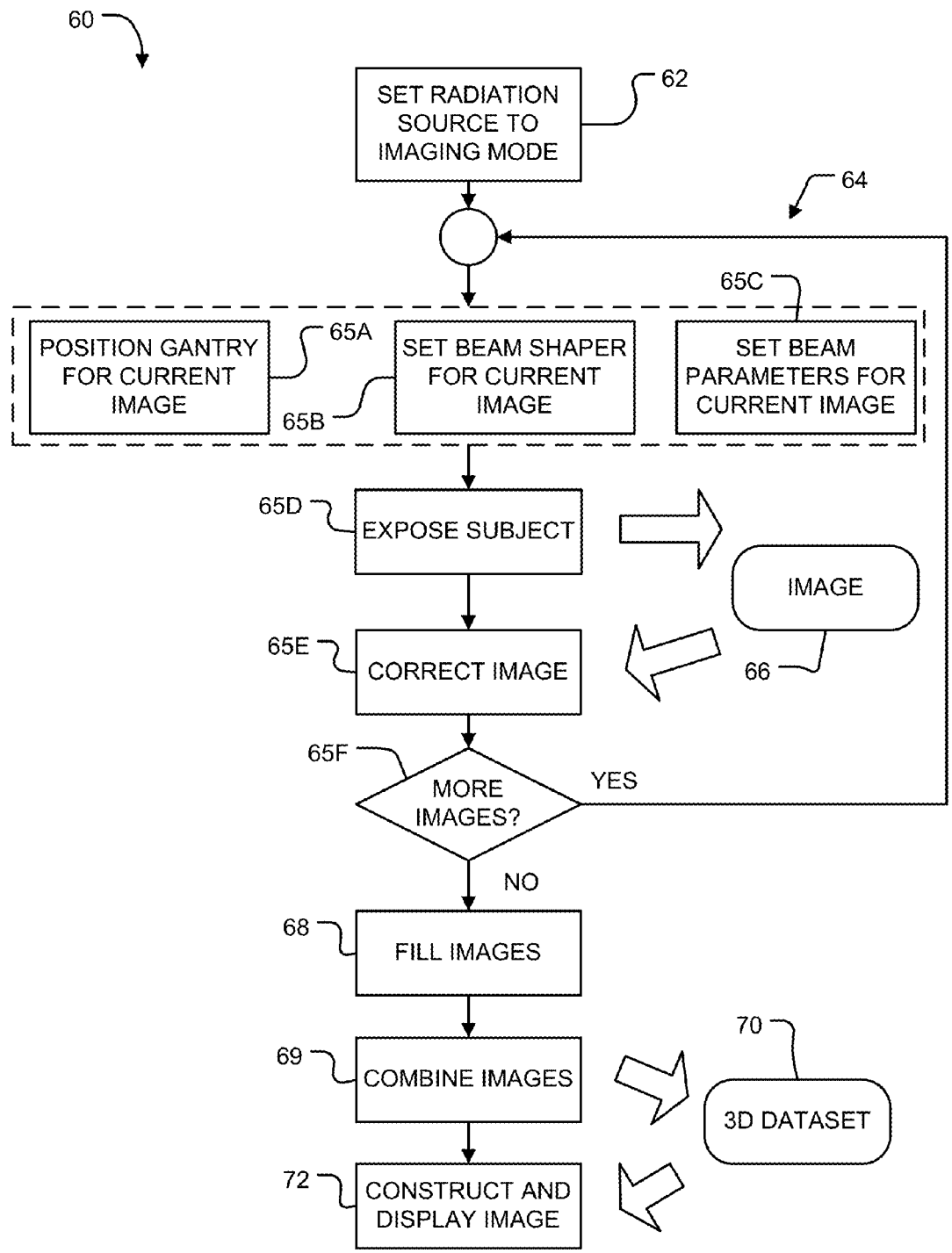
FIG. 3 is a flow chart illustrating an imaging method according to one embodiment.

FIG. 3 is a flow chart illustrating an imaging method 60 according to one embodiment. In block 62, method 60 sets a MV radiotherapy source into an imaging mode to deliver radiation for imaging. Block 62 may include, for example, replacing a high-Z target with a low-Z target, removing a flattening filter and setting the electron-beam energy for a linear accelerator. In some embodiments, in the imaging mode, 35% or more of the photons in the X-ray beam have energies in the range of 25 keV to 150 keV. Block 62 is optional in the case that the radiotherapy source is already appropriately set up.

Loop 64 acquires images from a desired number of gantry angles. In block 65A the gantry is positioned for the current image. In block 65B a beam shaper such as a multileaf collimator is set to shape an X-ray beam to the shape of a projection of the volume of interest. Block 65B may, for example comprise setting one or both of an angle of rotation of a multileaf collimator and leaf positions for leaves of the multileaf collimator. In block 65C, which is optional, beam parameters for the exposure are set. Block 65C may be useful in the case of an off-axis volume of interest in cases where the flux of X-ray beam 17 varies significantly across the beam. For example, when the volume of interest is located in a higher-flux portion of X-ray beam 17 electron beam current may be reduced below the current used when the volume of interest is located in a lower flux portion of X-ray beam 17. This can reduce the dose delivered to the subject.

In block 65D the subject is exposed to the shaped X-ray beam and an image 66 is acquired. In block 65E the image 66 is corrected to compensate for variations in the fluence of the imaging beam as well as variations in the sensitivity of the detector used to obtain images 66.

The corrections in block 65E may be based on previously-acquired calibration information that characterizes the X-ray beam. For example, prior to all image acquisition, dark field (IDF) and flood field (IFF) images may be acquired for image calibration. A dark field image is obtained without applying any beam to the imaging panel. A dark field image may be applied to correct for any variations of dark current between individual detector elements.

A flood field image may be acquired by exposing the entire sensitive area of the imaging panel to the beam and acquiring an image. A flood field image can be applied to correct for non-uniformities in the fluence of the imaging beam as well as for non-uniformity in detector response.

Any images acquired after IDF and IFF images may be corrected in software by subtracting the IDF image and dividing the result by the IFF image to produce a corrected image. In some embodiments correction is performed by computing the result:

$$IM_f = \frac{IM_i - IDF}{IFF} \quad (2)$$

where $IM_i$ is the uncorrected image data 66, $IM_f$ is the corrected image data and IDF and IFF are the dark field and light field images as defined above.

Block 65F determines whether more images are to be obtained. Block 68 fills the portions of each image 66 lying outside of the volume of interest with image data. Block 69 combines the filled images 66 to provide a 3D dataset 70. Block 69 may comprise back-projection of the images 66. Optionally block 69 comprises filtering images 66 prior to back-projecting images 66. Block 72 uses dataset 70 to construct and display an image. Block 72 may comprise, for example, constructing an image for coronal, sagittal or axial slices through the volume of interest.

Method 60 may be varied many ways. For example, blocks 65E and 68 may be performed inside or outside of loop 64. Where blocks 65E and 68 are performed inside loop 64 part or all of block 69 may also be performed in loop 64.

For clarity of explanation method 60 is described above as operating in a step-and-shoot mode with discrete motions of a gantry and beam shaper between imaging positions. The invention is not limited to step-and-shoot modes. The skilled reader will understand that imaging may be performed while the gantry is rotated continuously together with concurrent, synchronized, dynamic motion of the beam shaper. For example, a gantry may be driven to rotate through an arc without stopping while leaves of a multileaf collimator are driven to execute a dynamic sequence in tandem with the gantry motion. Images may be acquired at predetermined angles throughout the gantry rotation. Acquiring each image may comprise generating an imaging X-ray beam and operating an imaging X-ray detector.

One source of image data for filling the truncated images is previously-acquired CT data. It is almost always the case that a CT scan for a subject has been obtained for use in planning treatment for the subject prior to delivery of the treatment to the subject. In some embodiments image data for use in filling images 66 is obtained from such CT scan data (e.g. imaging data 43—see FIG. 1).

Figure 4:
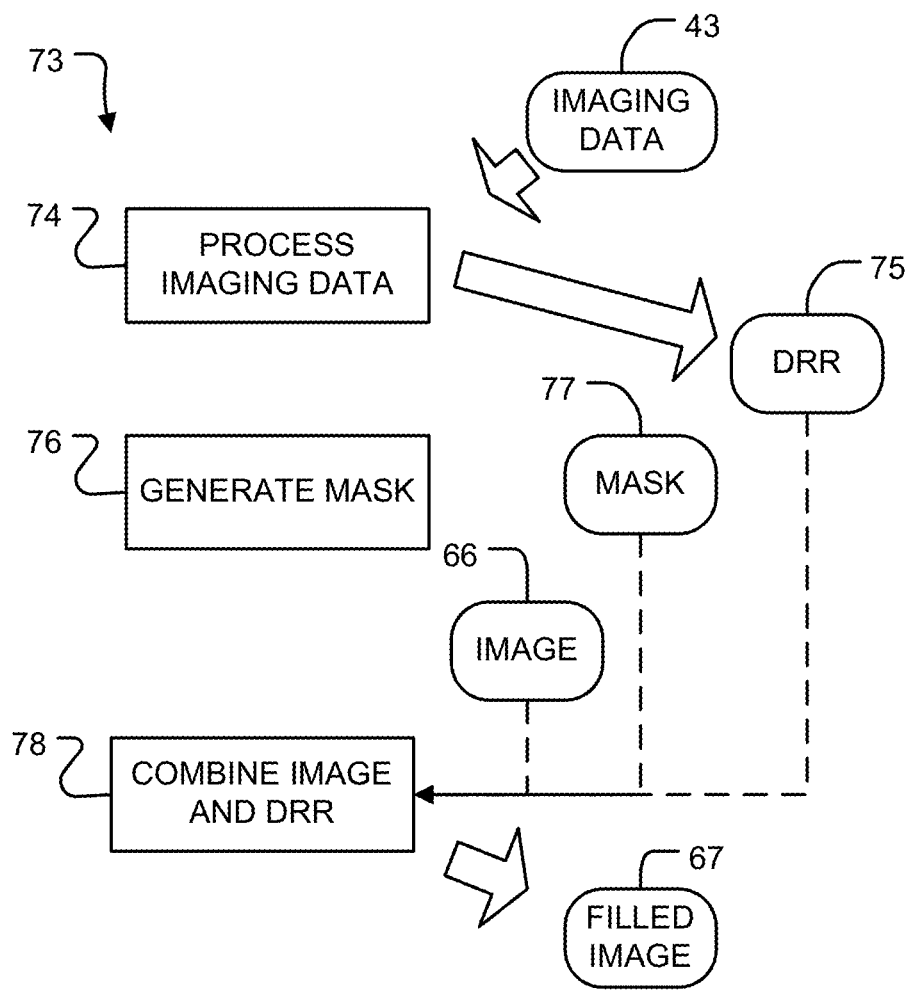
FIG. 4 is a flow chart illustrating an example method for filling images.

FIG. 4 illustrates an example method 73 for filling images 66. In block 74 imaging data 43 is processed to yield a digitally reconstructed radiograph (DRR) 75 from the point of view of the beam for the gantry angle corresponding to the current image 66. The DRR 75 is constructed based upon the geometry of the cone beam used for imaging. Low-Z target 50 may be (and for linear accelerators of the type in use in 2011 usually will not be) in the same location relative to the subject as high-Z target 16. Where low-Z target 50 is located closer to the subject than high-Z target 16 the low-Z imaging beam will gave greater divergence than the therapeutic beam. Also, photons from the low-Z target 50 will have substantially different energy spectral characteristics compared to a therapeutic beam. Algorithms for generating DRRs typically include the attenuation coefficient for photons, which depends on the incident spectrum (as well as the characteristics of the tissues through which the photons pass). Block 74 may implement an algorithm for generating DRR images 75 that takes into account these factors in order to produce DRRs 75 that closely match acquired low-Z images.

Some embodiments trade off between the quality of DRR 75 and the processing to generate DRR 75. A lower quality DRR 75 computed by applying a simplified algorithm may have quality sufficient for use in filling images 66. DRR 75 may be pre-computed and stored in which case block 74 may comprise retrieving the appropriate DRR 75 from a data store.

Block 76 generates a mask 77 corresponding to the projection of the volume of interest in the current image 66. Block 76 may, for example, identify as belonging to the volume of interest all pixels of image 66 having values exceeding a threshold or calculate a mask 77 from data defining the volume of interest. In an example embodiment mask 77 has the form of a binary image (pixel values are either 1 or 0). Mask 77 may be a negative of the projected volume of interest (for example, mask values may be set to 1 for pixels in which the pixel value from image 66 is less than a threshold and 0 otherwise). In alternative embodiments mask 77 may be a positive of the projected volume of interest.

Block 78 combines the image 66 with the corresponding DRR 75 using mask 77 to yield a filled image 67 which is the same as image 66 within the projected boundary of the volume of interest and is made up of image data from DRR 75 outside of the projected boundary of the volume of interest.

In an example embodiment mask 77 has the form of a binary image (pixel values are either 1 or 0). The mask 77 may be a negative of the projected volume of interest (for example, mask values may be set to 1 for pixels in which the pixel value from image 66 is less than a threshold and 0 otherwise). DRR 75 may be multiplied by mask 77 and the result may be added to image 66 to obtain a filled image 67.

Figure 5:
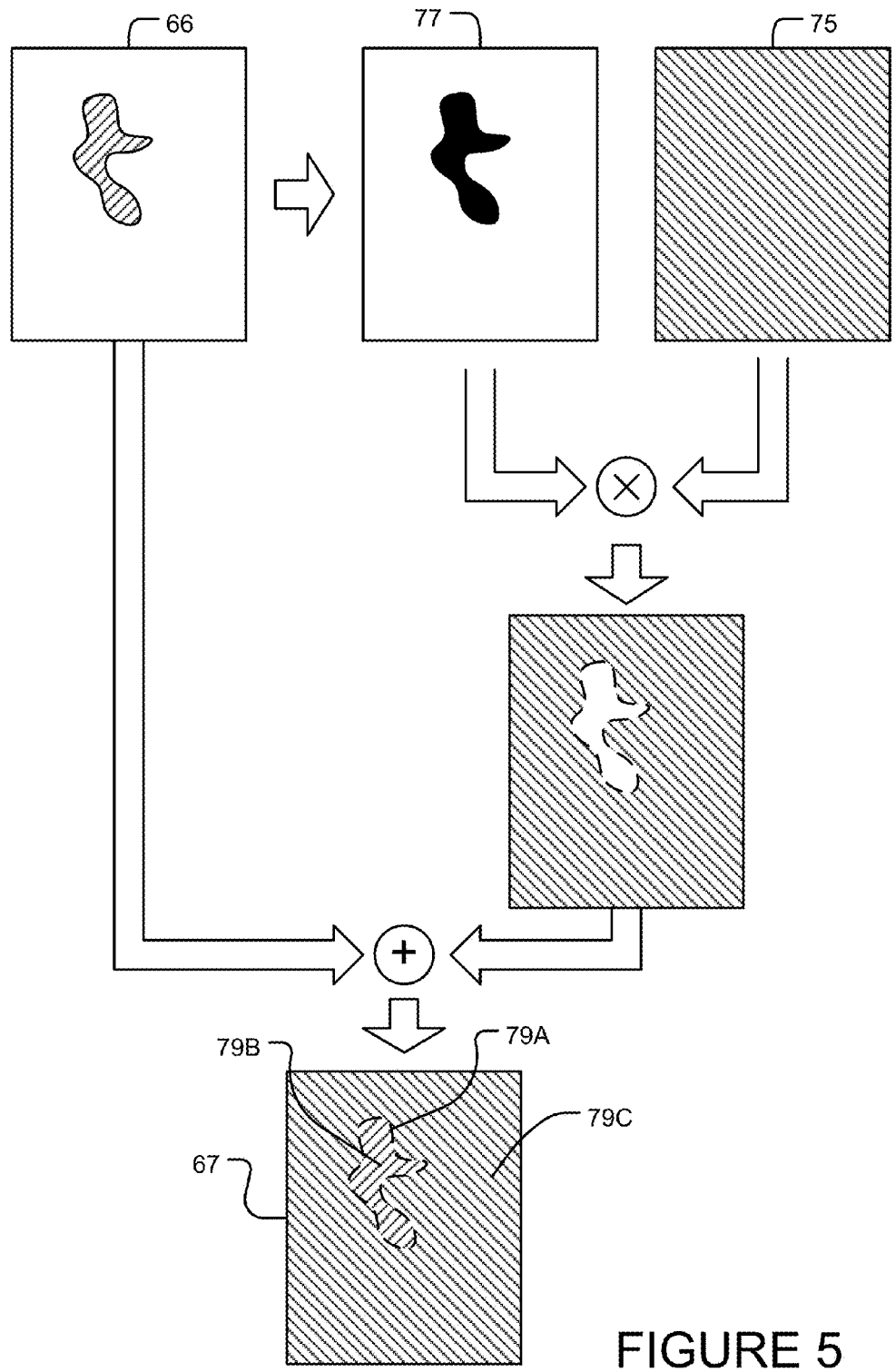
FIG. 5 illustrates an example image, a digitally-reconstructed radiograph (DRR) and a filled image.

FIG. 5 illustrates an example image 66, a DRR 75 a mask 77 and a filled image 67. In filled image 67 the boundary of the projected volume of interest is indicated by dashed line 79A, a region 79B inside boundary 79A comprises image data from image 66, a region 79C outside boundary 79A comprises image data from DRR 75.

Optionally pixel values in the image data used to fill truncated images 66 are matched to pixel values in adjacent pixels within the volume of interest of truncated images 66. For example, where the image data used to fill truncated images 66 includes the volume of interest, a correlation in pixel values can be established by comparing corresponding regions in the truncated image 66 and the DRR 75 or other image data being used for filling. For example, one may generate a tone mapping curve (or 'grey level transformation') by plotting the values of pixels in the truncated image versus the values of corresponding pixels in the filling image data and apply the tone mapping curve to modify the filling image data to better match the truncated image 66. The tone mapping curve may be parameterized by fitting a parameterized curve to the plotted curve.

Especially where images 66 are acquired for closely-spaced gantry angles it is not mandatory to calculate a separate DRR for filling every image 66. Optionally the same DRR may be reused to fill images 66 for two or more closely-spaced gantry angles. For example a separate DRR may be computed for the images 66 taken within a range of gantry rotation angles. The range may span 2 or 4 or 5 degrees for example or even larger angles such as 15 or 20 degrees.

Image data for use in filling images 66 may also be obtained by taking some images using unshaped (full-frame) X-ray beams or X-ray beams shaped to have boundaries outside of the projected boundary of the volume of interest. For example, one such images may be acquired for use in filling other images within a range of gantry angles. In an example embodiment N images 66 are acquired. An image 66 is acquired for every m degrees of gantry rotation over an angular range spanning (N−1)×m degrees. For example, an image may be acquired every 2 or 3 degrees of gantry rotation over a suitable range (e.g. a range spanning about 180 degrees-180 degrees plus the angle of the X-ray cone beam is ideal).

The X-ray cone beams used to acquire images 66 may be shaped to match the projected boundary of a volume of interest except that every $n^{th}$ image 66 may be a full-frame image. Each image 66 requiring fill may be filled using image data from the nearest full-frame image. In some embodiments full-frame images are only obtained for every 15 or 20 degrees or more of gantry rotation. In some embodiments, n is 5 or more or 10 or more.

In experiments done imaging a RANDO™ head phantom it was found that the quality of the portions of reconstructed images within the volume of interest was quite insensitive to the angular separation between full-frame images used for providing image data for fill. It was found that image quality in the region outside the volume of interest is compromised by sparse projection data. However, for many applications image quality in the region outside the volume of interest is unimportant.

Figure 6A:
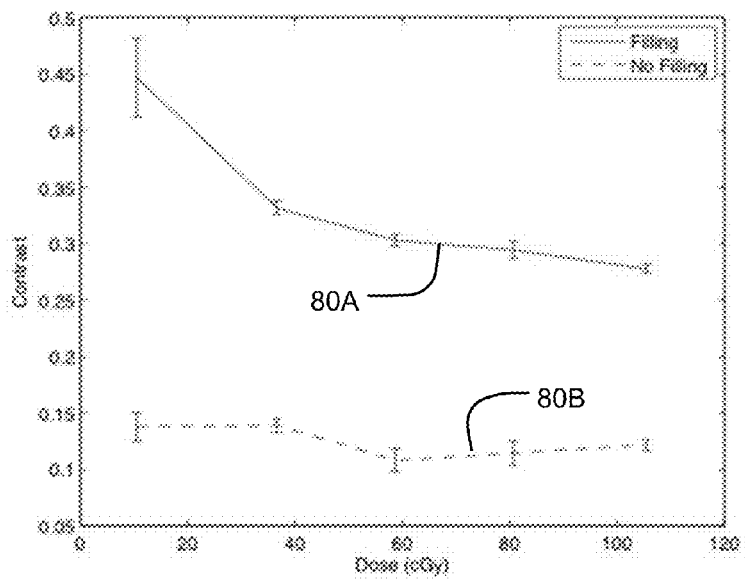
FIG. 6A is a graph showing contrast as a function of dose for CT results based on filled and unfilled images.
Figure 6B:
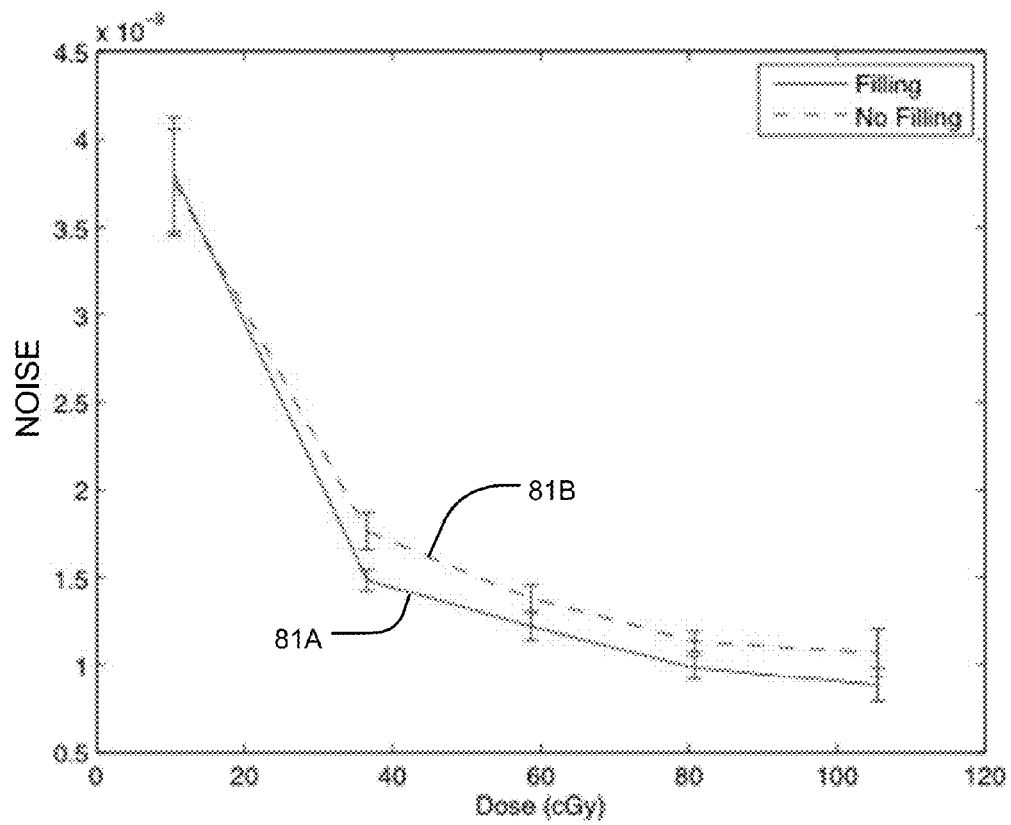
FIG. 6B is a graph showing noise as a function of dose for CT results based on filled and unfilled images.
Figure 6C:
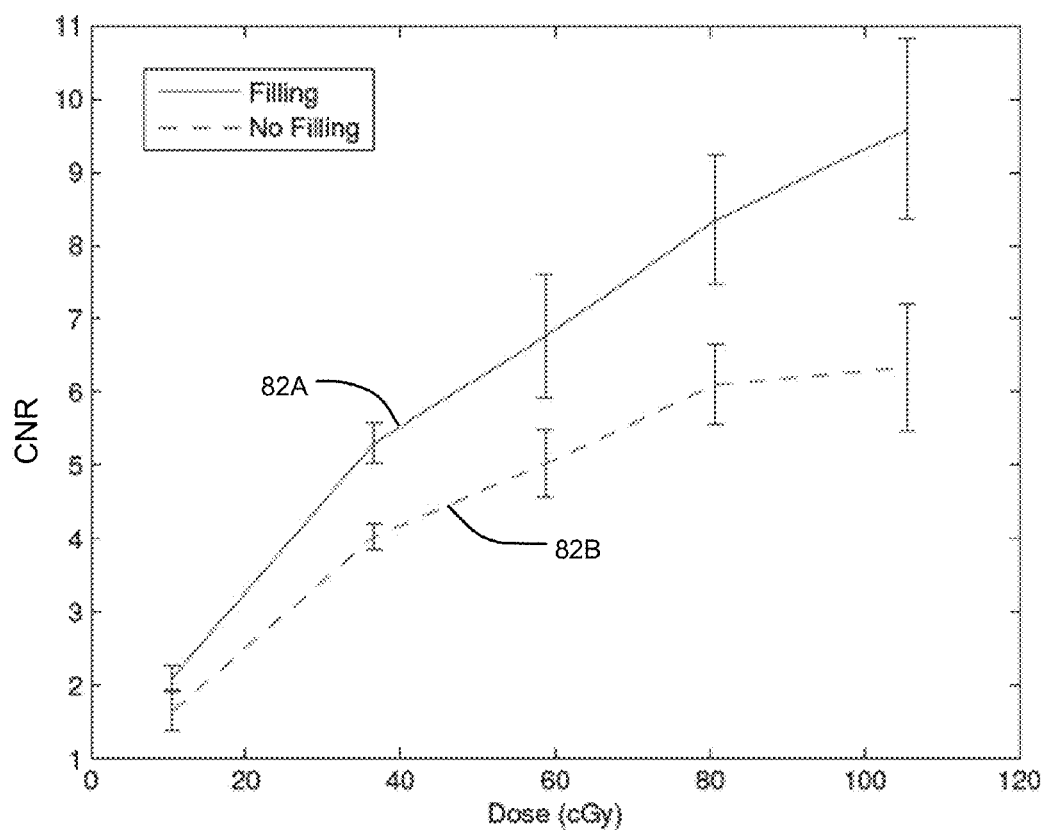
FIG. 6C is a graph showing CNR as a function of dose for CT results based on filled and unfilled images.

Although reducing artifacts is a main benefit of filling images 66, filling may provide some additional benefit as a result of improvement of CNR. FIG. 6A is a graph showing contrast as a function of dose for CT results based on filled (curve 80A) and unfilled (curve 80B) images. FIG. 6B is a graph showing noise as a function of dose for CT results based on filled (curve 81A) and unfilled (curve 81B) images. FIG. 6C is a graph showing CNR as a function of dose for CT results based on filled (curve 82A) and unfilled (curve 82B) images.

Other types of image reconstruction are also possible. For example, images may be reconstructed using pi-line reconstruction as described in Zou Y. et al. *Exact image reconstruction on PI-lines from minimum data in helical cone-beam CT* Phys Med Biol. 2004 Mar. 21; 49(6):941-59 which is hereby incorporated by reference herein. Such reconstructions may be used in some embodiments.

The data on which FIGS. 6A, 6B, and 6C are based was for a beam shaped using a 10 cm aperture. Fill was provided from full-field images having a width of 26 cm. One full field image was obtained for each 20 degrees of gantry rotation. Truncated images were filled using image data from the closest full-field image.

The imaged subject was a bone object in a uniformly cylindrical water phantom. It can be seen that filling the images beneficially increases contrast and decreases noise. Thus, CBCT data of a desired quality can be obtained for at least some subjects with lower radiation doses when CBCT images are filled than when the images are subjected to CT processing without being filled.

Figure 7A:
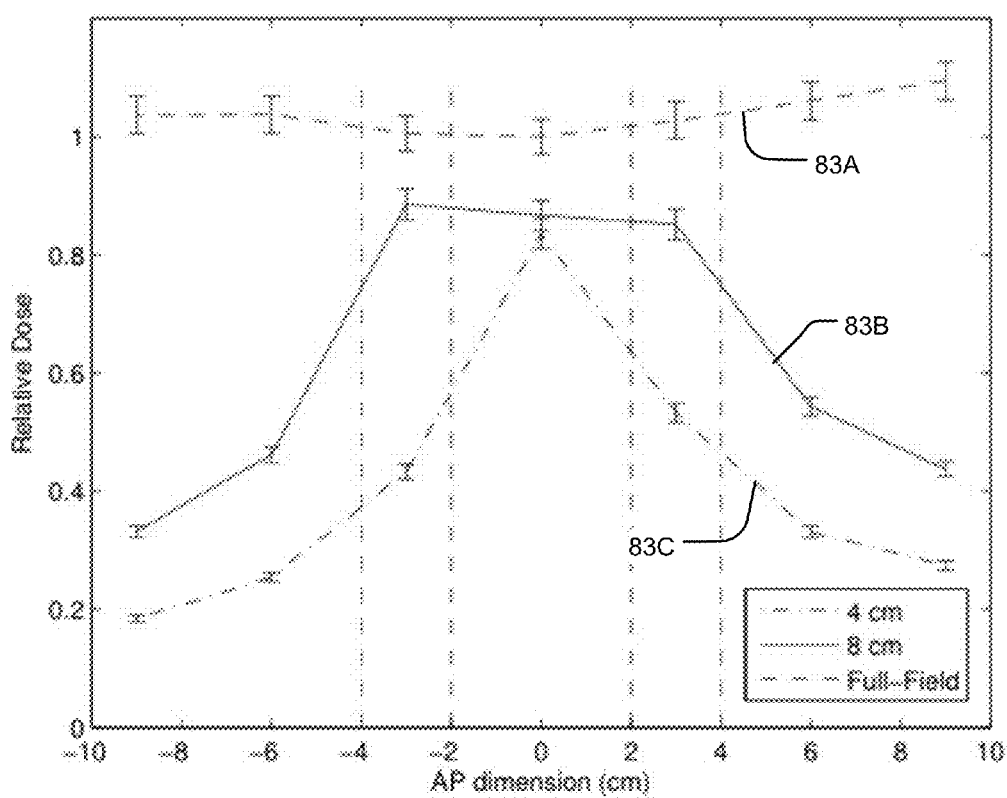
FIGS. 7A and 7B illustrate dose from an imaging exposure to cone-beam X-ray radiation as a function of position for 4 cm diameter and 8 cm diameter cylindrical volumes of interest.
Figure 7B:
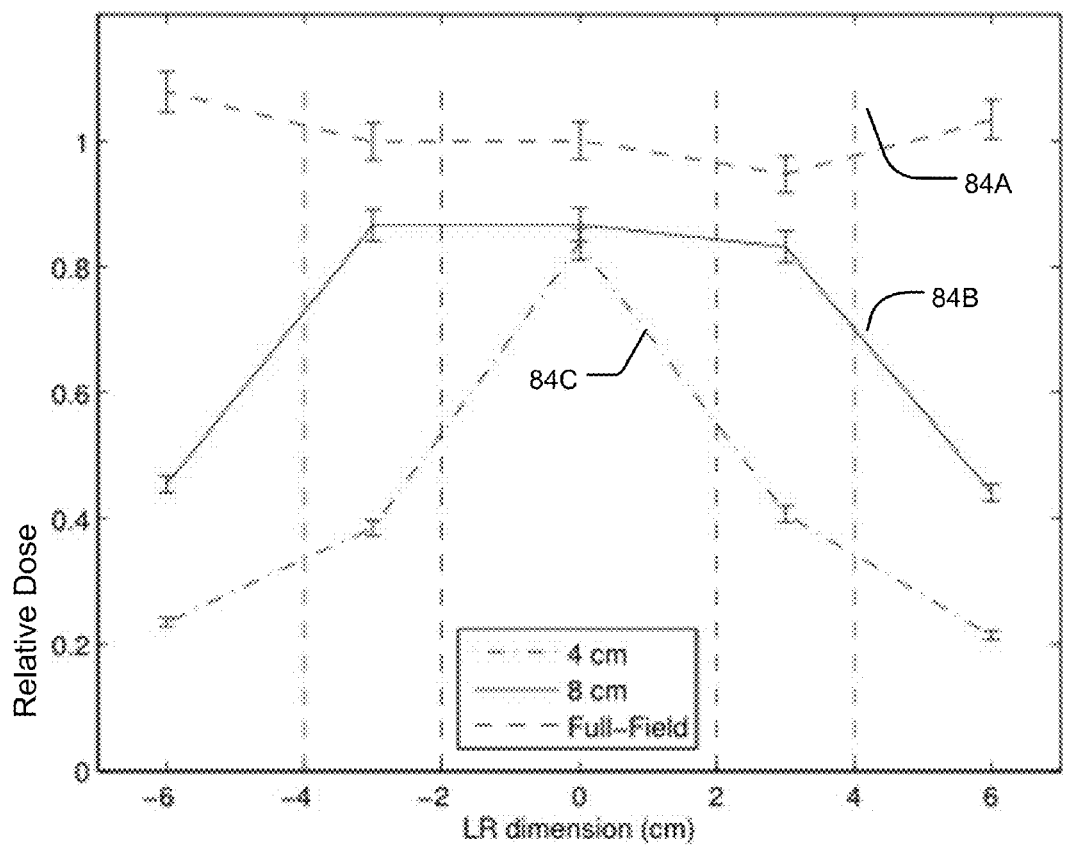

FIGS. 7A and 7B illustrate dose from an imaging exposure to cone-beam X-ray radiation as a function of position for 4 cm diameter and 8 cm diameter cylindrical volumes of interest. The doses plotted in FIGS. 7A and 7B were measured using thermoluminescent dosimeters inside a phantom. FIG. 7A shows dose as a function of position in an anterior-posterior direction in a saggital plane through the volume of interest. Curve 83A is dose for a full-field image. Curve 83B is dose for a volume of interest 8 cm in diameter. Curve 83C is dose for a volume of interest 4 cm in diameter. FIG. 7B shows dose as a function of position in a left-right direction in a coronal plane through the volume of interest. Curve 84A is dose for a full-field image. Curve 84B is dose for a volume of interest 8 cm in diameter. Curve 84C is dose for a volume of interest 4 cm in diameter.

Repositioning the leaves of a multileaf collimator takes some time. Larger movements typically require longer times. To reduce the time required for obtaining full-field images and images using X-ray beams shaped to conform to regions of interest one can acquire a number of full-field images and then acquire a number of images using shaped X-ray beams. For example, one could move the gantry through a range of angles in one direction while obtaining full-field images and then move the gantry again through the range of motion while acquiring images using shaped X-ray beams.

In an example embodiment, the gantry acquires images 66 using shaped X-ray beams as it is moved through about 180 degrees. Subsequently the direction of gantry rotation is reversed and full-field images are acquired as the gantry is moved back through the angular range. In the alternative, full field images can be acquired first and images can then be acquired using a shaped beam. In another example embodiment the gantry is rotated through 360 degrees and the MLC is controlled to shape the X-ray beam for images taken in a ½ rotation of the gantry and to obtain full-frame images in the other ½ rotation of the gantry.

Another option for filling images 66 is to fill image areas outside of the volume of interest by extrapolation from image areas inside the volume of interest. This may be done on a line-by-line basis, for example. A fitting function such as a polynomial function may be fit to pixel values inside an image area corresponding to a volume of interest. Pixel values for image areas outside the volume of interest can then be set according to the fitting function. The fitting function may be chosen to avoid sharp discontinuity at the boundary of the part of the image corresponding to the volume of interest. The fitting function may be a lower order polynomial function for example.

As a simpler alternative to shaping the X-ray beam to conform with a volume of interest, truncated images may be obtained by shaping the X-ray beam with a predetermined on-axis shape that is the same for all apertures (i.e. the same for each image 66). The shape could, for example, be a circle, ellipse, oval or other rounded shape, a stripe or rectangle or the like.

An advantage of VOI CBCT image acquisition is that radiation dose is reduced not only outside of the volume of interest (i.e. in largely-shielded patient volumes) but also within the volume of interest itself. This advantage arises where a beam is shaped using apertures that are small relative to full-field acquisition. In such cases the contribution to the dose delivered to the volume of interest by photons scattered from outside of the volume of interest is reduced. This effect of beam shaping is especially significant for low-Z imaging beams because in such X-ray beams (which have lower effective beam energies than beams generated from a high-Z target), the proportion of scattered photons tends to be higher relative to primary photons. The reduction of scattered photons can improve aspects of image quality as compared to full field imaging since scatter degrades both contrast and spatial resolution.

It can be appreciated that some embodiments of the imaging apparatus described above offer the advantage that imaging can be performed in a manner that is tightly integrated with the delivery of therapeutic radiation. No auxiliary imaging system is required. Associated overhead in terms of cost and quality assurance are reduced. A further advantage offered by some embodiments is that the imaging and therapeutic beams are coaxial and so a beam's-eye-view image for the imaging beam is also a beam's-eye-view image from the perspective of the therapeutic beam.

In some embodiments, imaging as described herein may be performed simultaneously for a plurality of different volumes of interest. The different volumes of interest may be disconnected from one another or may be contiguous or even overlap.

Figure 8A:
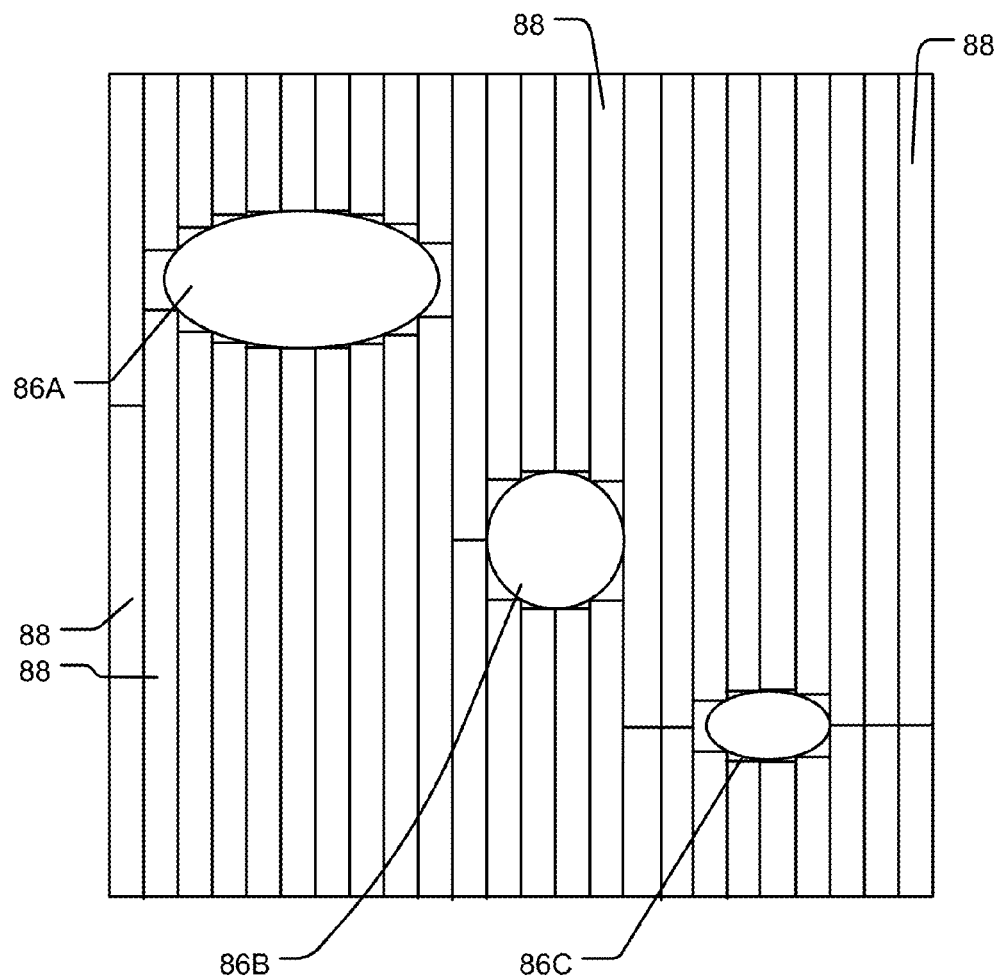
FIG. 8A shows a beam's-eye view of a plurality of volumes of interest projected into the plane of a multileaf collimator.

Depending upon the capabilities of a beam shaper (e.g. a MLC) it may be possible to obtain images 66 using beams that are shaped to expose a plurality of volumes of interest while reducing or substantially eliminating exposure to radiation outside of the regions of interest. For example, FIG. 8A shows a beam's-eye view of a plurality of volumes of interest 86A, 86B, and 86C projected into the plane of a multileaf collimator and shows positions of leaves 88 of the multileaf collimator that would shape an X-ray cone beam to expose the volumes of interest. Where the plural volumes of interest have sizes and locations such that a multileaf collimator can be controlled to shape the X-ray beam to expose the plural volumes of interest then imaging the plural volumes of interest may be performed as described above.

Figure 8B:
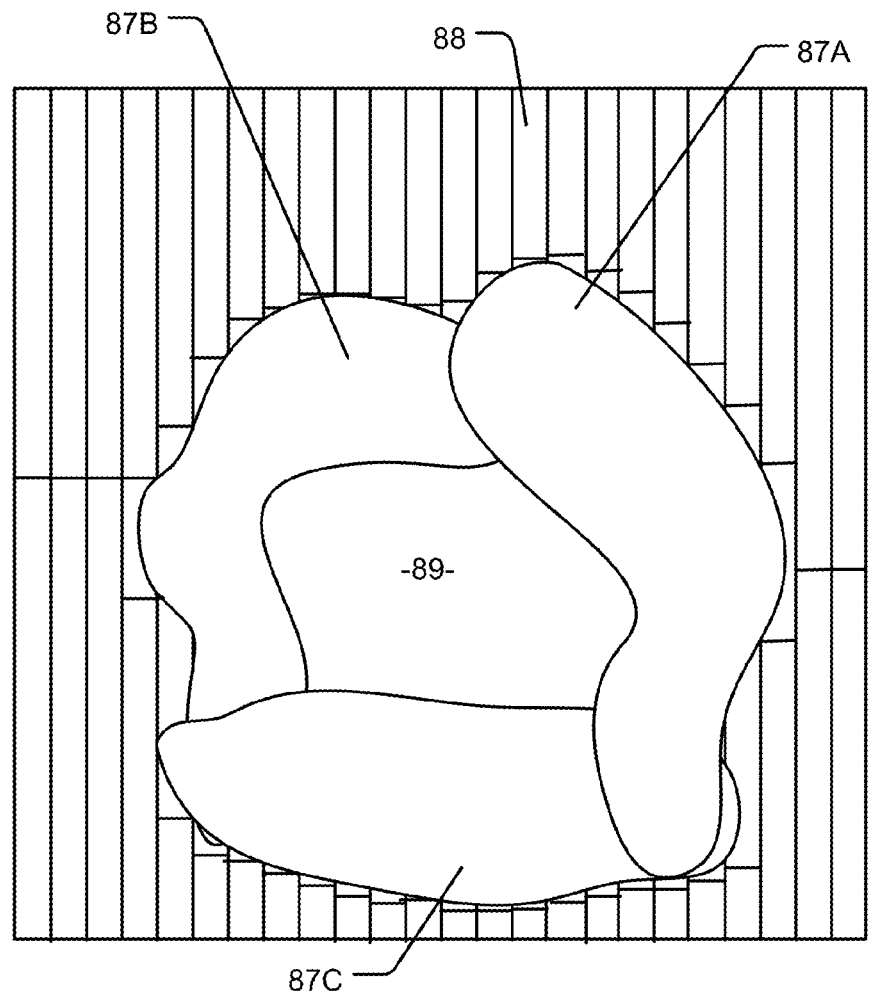
FIG. 8B is an example of an arrangement of volumes of interest viewed from an angle for which it is impossible to use a multileaf collimator to shape an X-ray beam to match the projection of the volumes of interest.

In cases where the multileaf collimator or other beam shaper cannot be controlled to shape the X-ray beam appropriately then the plural volumes of interest may be imaged using a plurality of apertures. FIG. 8B is an example of an arrangement of volumes of interest 87A, 87B, and 87C (collectively volumes 87) viewed from an angle for which it is impossible to use a multileaf collimator to shape an X-ray beam to match the projection of the volumes of interest. This is because to block radiation from central area 89, at least some leaves 88 of the multileaf collimator would need to also block radiation from reaching one or more of the volumes of interest 87.

Figure 8C:
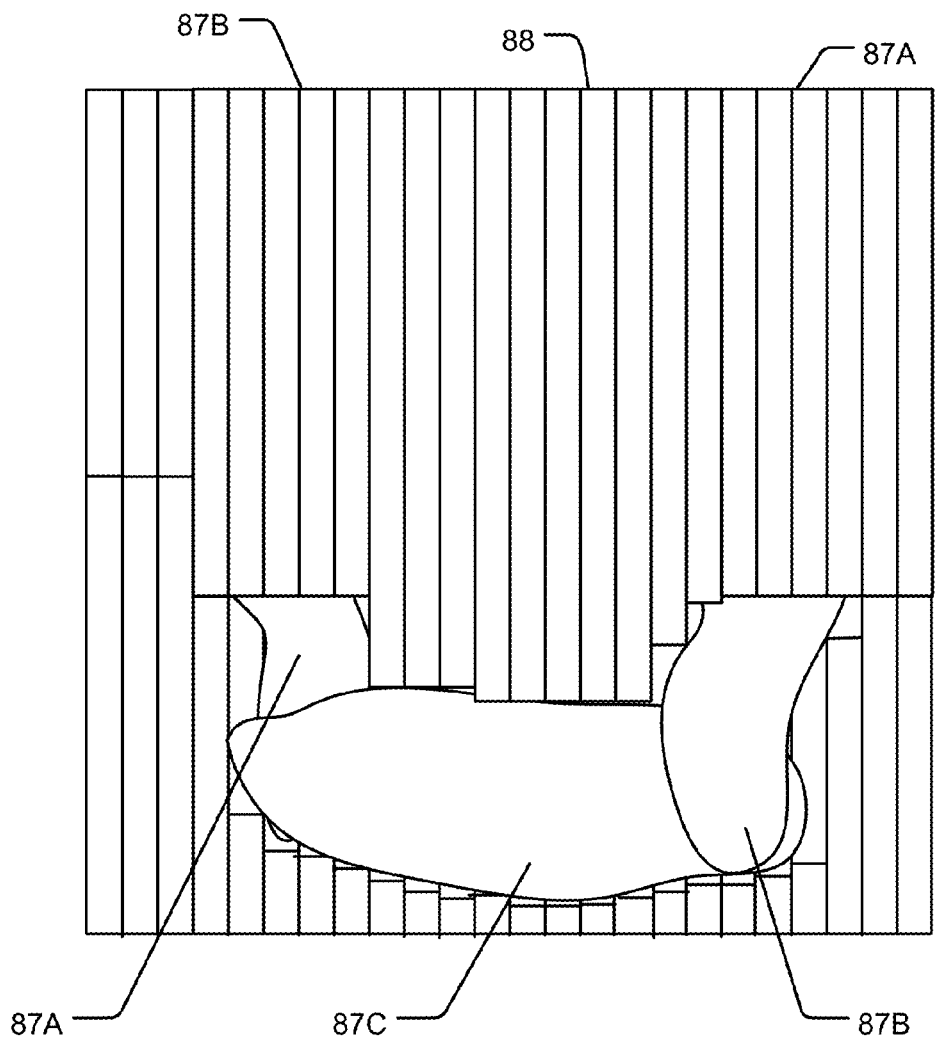
FIGS. 8C and 8D illustrate two different configurations of the leaves of a multileaf collimator.
Figure 8D:
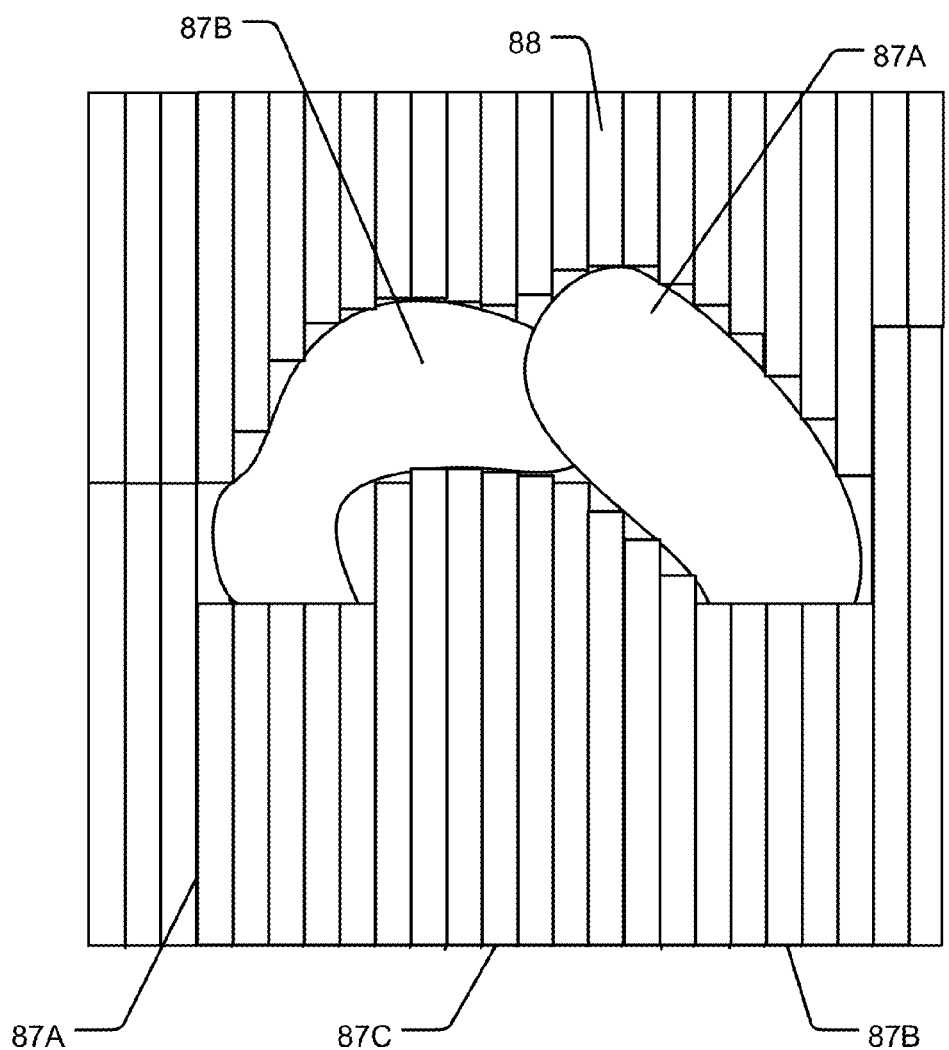

In such cases images 66 can be acquired using two or more X-ray beam shapes and then combining the resulting images. For example, FIGS. 8C and 8D illustrate two different configurations of the leaves 88 of a multileaf collimator. Two images obtained using X-ray beams shaped by these configurations will image the volumes of interest 87 but, each of the X-ray beams is shaped to avoid exposure outside of volumes of interest 87.

In some embodiments a multileaf collimator is rotated about its own axis to allow leaves 88 to be adjusted to better match the contours of the boundaries of the projections of volumes of interest.

Figure 9A:
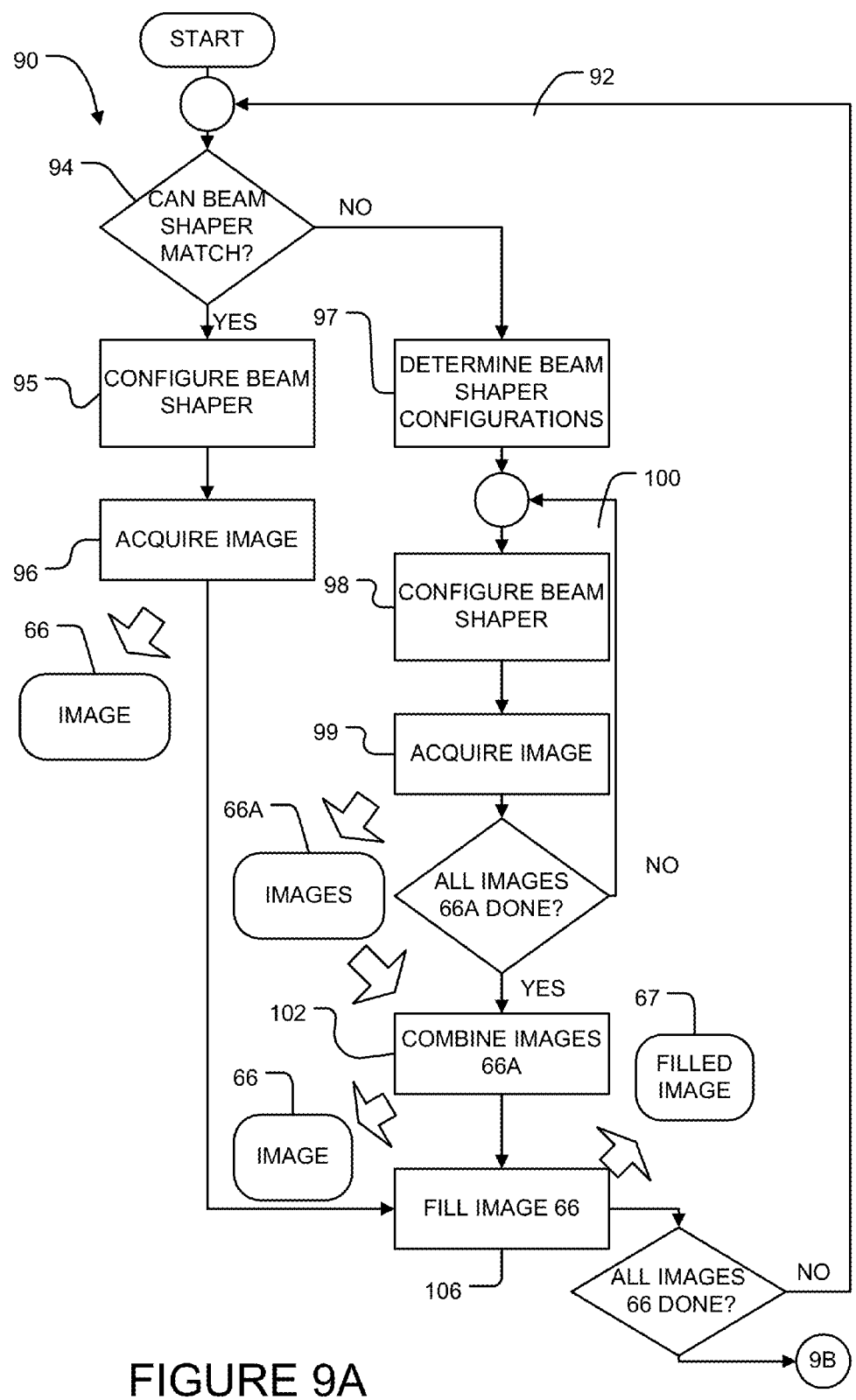
FIGS. 9A and 9B are a flow chart illustrating a method for obtaining 3D image data covering multiple volumes of interest.
Figure 9B:
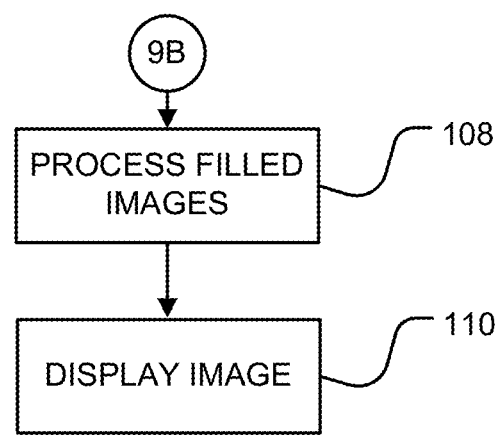

FIG. 9 illustrates a method 90 for obtaining 3D image data covering multiple volumes of interest. Loop 92 is repeated for a plurality of gantry angles that are spaced apart by a suitable angular distance. Block 94 determines whether the beam shaper can be configured to shape the X-ray beam to conform with the projection of the volumes of interest for the current angle. If so (YES result), block 95 configures the beam shaper to shape the X-ray beam and block 96 acquires an image 66.

If block 94 determines that it is not possible to configure the beam shaper to shape the X-ray beam to conform with the projection of the volumes of interest for the current angle (NO result) then block 97 determines a plurality of beam shaper configurations that each shape the X-ray beam to expose a portion of the projections of volumes of interest. In aggregate, the volumes of interest are all exposed by exposures using made using the plural beam shaper configurations and radiation is blocked from other areas. Block 98 configures the beam shaper to shape the X-ray beam according to a current one of the configurations and block 99 acquires an image 66A. Loop 100 is repeated until images 66A have been obtained using X-ray beams shaped by each of the configurations determined by block 97.

Block 102 combines images 66A into an image 66. Block 102 may comprise, for example, setting all pixel values in images 66A that are below a threshold value to zero and then summing the images 66A.

Block 106 fills images 66 as described above. Block 108 processes the filled images 67 to provide a 3D data structure. Block 110 recreates and displays an image in a plane passing through one or more of the volumes of interest based on the 3D data structure. Block 110 optionally displays highlighting, lines or other indicia indicating boundaries of the volumes of interest on the displayed images.

It is not necessary that all volumes of interest be imaged in the same image quality. Some volumes of interest may be imaged using higher doses than other volumes of interest. For example, a particular volume of interest (e.g. a target volume for radiotherapy and its immediate margin) may be imaged with a dose sufficient to provide a relatively high contrast-to-noise ratio while simultaneously capturing the external surface of the patient at lower CNR.

Imaging different volumes of interest with different doses may be achieved in various ways. One approach is to image different volumes of interest using different apertures (different beam shaping). Exposure in each aperture may then be controlled to achieve a desired image quality in the volume(s) of interest corresponding to the aperture. Another approach is to image a second volume of interest in fewer apertures than a first volume of interest. This may be achieved, for example, by shaping an imaging beam to image the first volume of interest for a number of steps of gantry rotation and opening the aperture to include the second volume of interest for only some of the gantry rotation angles. For example, a full-field exposure could be taken at every $n^{th}$ gantry rotation step while exposures at other gantry rotation steps may be limited by shaping the beam to conform with the projection of the first volume of interest. Such full-field exposures may also be used as a source of fill image data as described above. These two approaches may be combined.

Apparatus and methods according to some embodiments calculate volumetric radiation doses delivered during imaging. The imaging radiation doses may be included in radiation dose estimates being used by a treatment planning system. In some embodiments a treatment planning system is configured to optimize a radiation treatment plan based upon dose estimates that include radiation dose delivered during imaging. Such embodiments may but do not necessarily apply the imaging methods as described above. In some embodiments doses from other imaging modes (e.g. MV CBCT) may be included in dose estimates used in optimizing a treatment plan.

Calculating dose delivered by imaging or therapeutic beams typically requires knowledge of the location of the external surface of the subject (e.g. the location of the subject's skin surface) since the dose calculation should take into account attenuation of the beam with depth. In some embodiments where it is desired to estimate an imaging dose based on VOI CBCT images, or to recalculate a dose of therapeutic radiation based on VOI CBCT images, a volume of interest that includes the subject's skin surface may be imaged using a relatively low dose. It may be sufficient to have image quality just good enough to determine the location of the external surface of the subject. For example, a volume of interest centered on a target volume can image the target volume at high quality while an outer volume that includes the external surface of the subject can be imaged at lower quality and dose as described above.

In some embodiments, the external region including the subject's external surface is post processed to reduce noise. Image details for accurate dose estimation may be sourced from planning CT data and fitted to the external region by deformable co-registration.

In embodiments where imaging is not performed using the same beam used for radiation therapy then the treatment planning system and radiotherapy apparatus may be commissioned and validated for both the radiotherapy beam and the imaging beam. For example, apparatus may be commissioned for both a treatment beam generated using a high-Z target flattened using a flattening filter and an imaging beam generated using a low-Z target and no flattening filter. The commissioning may reflect differences in the geometries of the imaging and treatment beams as well as differences in the spectral makeup of the imaging and treatment beams.

Figure 10:
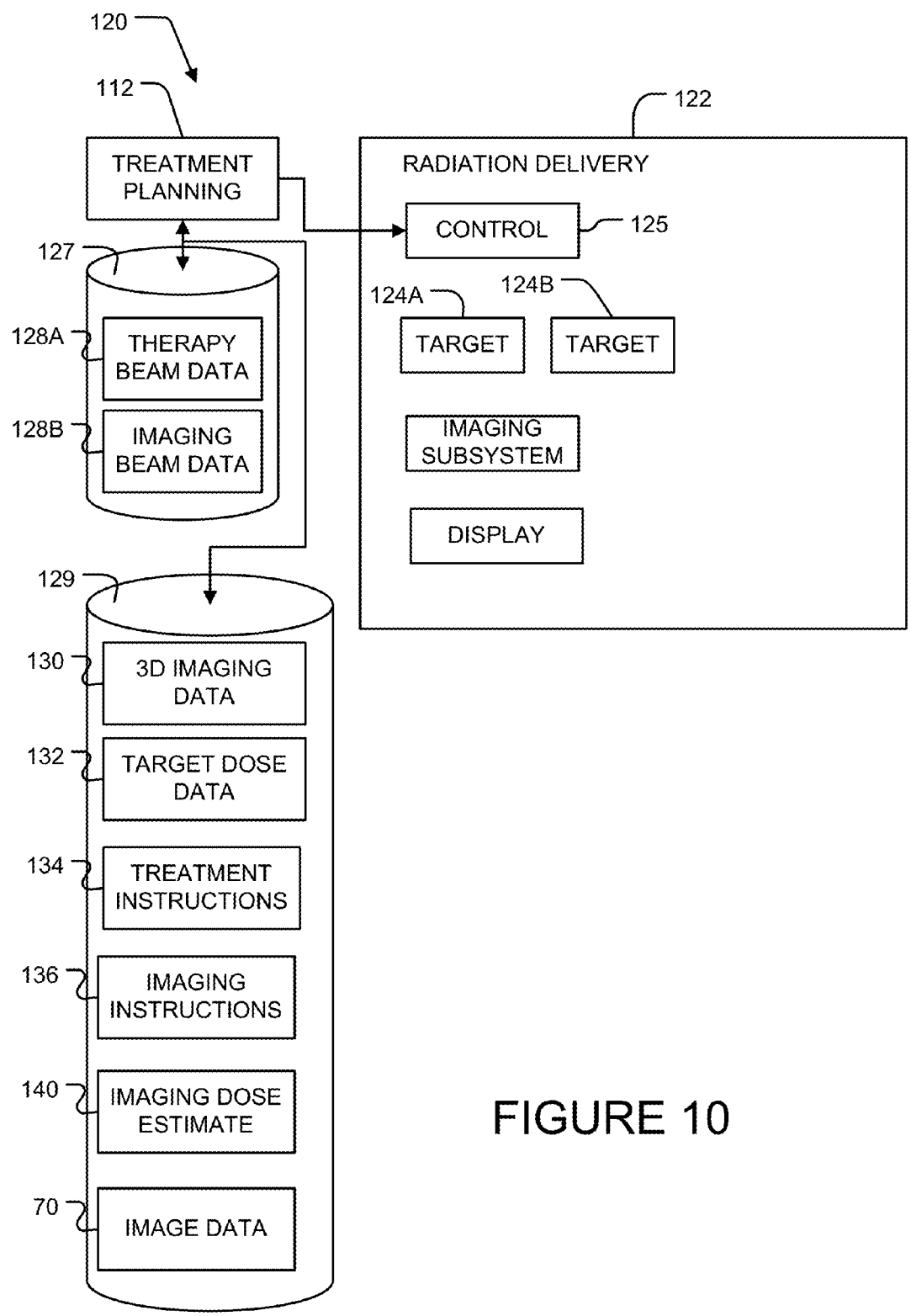
FIG. 10 is a block diagram of a radiotherapy system that includes a treatment planning unit operating in conjunction with a radiation delivery machine.

FIG. 10 is a block diagram of a radiotherapy system 120 that includes a treatment planning unit 112 operating in conjunction with a radiation delivery machine 122. Radiation delivery machine 122 may comprise, for example, a linear accelerator.

Radiation delivery machine 122 comprises interchangeable targets 124A and 124B. A controller 125 is connected to configure radiation delivery machine 122 to deliver a therapy beam using target 124A or an imaging beam using target 124B.

Treatment planning unit 112 has access to a data store 127 containing data 128A and 128B that respectively characterize the therapy beam and the imaging beam. Treatment planning unit 112 has access to a data store 129 (which may be part of data store 127 or separate from data store 127) containing 3D imaging data 130 for a subject. 3D imaging data 130 may include data acquired from one or more of CT scanning, magnetic resonance imaging (MRI), positron emission tomography (PET), ultrasound scans or other imaging modalities.

An operator can work with treatment planning unit 112 to establish a target radiation dose distribution. For example, the desired target dose distribution may be essentially constant inside a tumor in the subject and zero (or as close to zero as possible) in normal tissues surrounding the tumor. The operator may view images generated from images 3D imaging data 130 for assistance in specifying the target dose distribution. In the illustrated embodiment target dose distribution data 132 specifies the target dose distribution calculated by treatment planning unit 112.

The operator can work with treatment planning unit 112 to establish a treatment plan that attempts to efficiently and accurately deliver the target radiation dose distribution as specified by target dose distribution data 132. The treatment plan comprises instructions 134 that can be executed by controller 125 of radiation delivery machine 122 to deliver radiation to the subject. Instructions 134 may comprise, for example instructions identifying gantry angles, beam shaper settings (e.g. leaf positions and rotation angles for a multileaf collimator, jaw positions, etc.) and beam conditions (e.g. accelerator energy and fluence). The instructions may specify a step-and-shoot mode of radiation delivery and/or dynamic modes of radiation delivery.

A treatment plan may provide for delivery of the radiation in a number of fractions. The fractions may be delivered at intervals (for example one fraction per day, one fraction every few days or one fraction every several hours). The interval between fractions typically depends upon the condition being treated and the treatment approach decided upon by the managing physician in consultation with the subject. Each fraction may comprise irradiation from a number of gantry angles with radiation that is shaped in one or more ways at each gantry angle. Some treatment plans involve many fractions and are designed to be executed over a period of days or weeks. Other treatment plans are designed to be executed over shorter periods. Some treatments, such as certain radiosurgery treatments can be executed by delivering a single fraction.

Various approaches to treatment planning are known to those of skill in the art. Treatment planning systems for radiation therapy are commercially available. One example is the ECLIPSE™ treatment planning system available from Varian Medical Systems of Palo Alto, Calif. Treatment planning unit 112 may comprise an add-on to an existing treatment planning system or a stand-alone treatment planning system, for example.

Treatment planning unit 112 is configured to develop one or more imaging sequences in conjunction with a treatment plan. The imaging sequences may, for example, be used to verify that the subject is properly positioned for the delivery of each fraction. It is necessary to ensure that the subject is in the proper position relative to radiation delivery machine 122 for each fraction. In an example embodiment, a treatment plan may include an imaging sequence at the beginning of each fraction. After one or more volumes of interest have been identified the imaging sequence for imaging those volumes of interest may be automatically generated and added to the treatment plan to be executed before each fraction or before certain fractions.

The imaging sequence may specify acquisition of images over a full gantry rotation, gantry rotation of about 180 degrees (e.g. 180 degrees plus the angle of the X-ray cone beam). Other angular ranges may also be used depending on the application. For example, methods and apparatus as described herein may be applied in 'tomosynthesis', a technique in which a narrow rotational range is selected in order to reconstruct an image in a desired, single plane through the subject. The small range of angles is chosen based on the desired image plane. For example, one could acquire data to reconstruct just the sagittal or just the coronal plane of the subject by acquiring projections in a narrow range around that plane. Methods and apparatus as described herein may be applied, for example to provide a low-Z VOI tomosynthesis.

In some embodiments the imaging sequences comprise instructions that can be executed by controller 125 of radiation delivery machine 122 to place radiation delivery machine 122 in an imaging mode, deliver imaging radiation to the subject, and trigger an imaging detector to collect image data for each image. The instructions may comprise, for example instructions identifying gantry angles, beam shaper settings (e.g. leaf positions and rotation angles for a multileaf collimator, jaw positions, etc.) and beam conditions (e.g. accelerator energy and fluence). In some embodiments the instructions specify beam shapes for the acquisition of images for one or more volumes of interest as described above.

In some embodiments the instructions specify different beams for imaging and treatment. The beams may differ, for example in terms of energy spectra and/or geometry. In some embodiments, imaging beams and treatment beams are both generated using a MV electron beam from the same linear accelerator. FIG. 10 shows imaging instructions 136. Imaging instructions 136 may be combined with or separate from treatment instructions 134.

Treatment planning unit 112 may be configured to estimate a 3D imaging dose distribution 140 that will be delivered to the subject upon execution of the imaging sequence. 3D imaging dose distribution 140 may be used in the optimization or re-optimization of a treatment plan.

Figure 11:
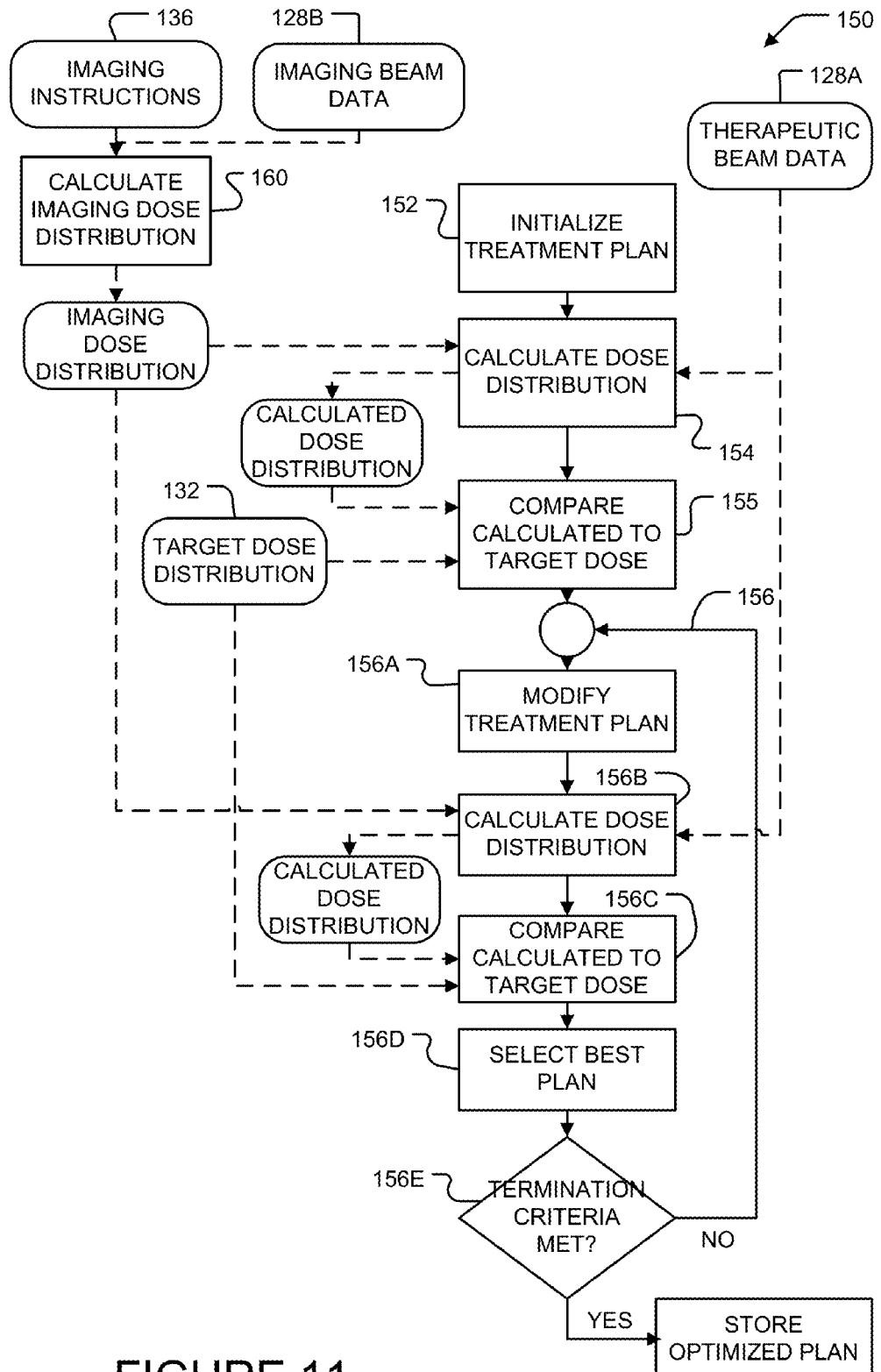
FIG. 11 illustrates one method for using a 3D imaging dose distribution in the optimization of a treatment plan.

FIG. 11 illustrates one method 150 for using a 3D imaging dose distribution in the optimization of a treatment plan. In block 152 a treatment plan is initialized. In block 154 the dose distribution that would be delivered by the initial treatment plan is calculated using data 128A that characterizes a therapeutic beam to be used in executing the treatment plan. In block 155 the dose distribution of block 154 is compared to the target dose distribution 132.

Method 150 includes an optimization loop 156. In block 156A the treatment plan is modified. The modification may be stochastic or determined according to another optimization methodology.

In block 156B the dose distribution that would be delivered by the modified treatment plan is calculated using data 128A. In block 156C the dose distribution of block 156B is compared to the target dose distribution 132. Block 156D determines whether the treatment plan as modified in block 156A is better than the treatment plan prior to modification by block 156A (e.g. the modified treatment plan satisfies relevant criteria and a the comparison of block 156C indicates a dose distribution that is closer to target dose distribution 132). Block 156D keeps the better of the modified treatment plan and the treatment plan prior to modification by block 156A. Block 156E determines whether a termination condition is satisfied. If so (YES result) optimization loop 156 ends. Otherwise (NO result) processing continues at block 156A. In block 158 the optimized treatment plan is stored.

Method 150 includes block 160 that calculates 3D imaging dose distribution 140 from previously established imaging instructions 136 and data 128B characterizing an imaging beam. Blocks 154 and 156C add all or parts of imaging dose distribution 140 to the dose distributions estimated for the treatment plan.

A wide variety of computer-implemented treatment planning algorithms are known and described in the patent and technical literature. It is typical that such algorithms include optimization steps in which a dose distribution is estimated and, based upon the estimated dose distribution (usually based on a comparison of the estimated dose distribution to a target dose distribution), further optimization steps are performed. Many such algorithms are inverse planning algorithms which start with a desired radiation dose distribution and attempt to establish a treatment plan (set of instructions for a radiation delivery system) that will deliver the desired radiation dose distribution to the subject.

One non-limiting aspect of the present invention is to provide new computer-implemented treatment planning algorithms and systems by modifying such existing algorithms by: determining an imaging radiation dose, as described herein and including that imaging radiation dose in the estimated dose distributions used by the treatment planning algorithm—thereby arriving at a treatment plan in which the imaging dose is counted as contributing to the therapeutic dose and the treatment plan is optimized taking into account a dose expected from imaging during delivery of the treatment.

Some embodiments provide an automated treatment planning system that receives an imaging volume from a user. The imaging volume may, for example, be defined relative to previously-obtained imaging data for the subject. The previously-obtained imaging data may comprise data from a CT scan, MRI or other imaging modality or modalities, for example. The treatment planning system also receives from a user information specifying an imaging frequency (e.g. once per fraction, once per day, once every two days or the like). Optionally the treatment planning system receives from a user information specifying a required imaging quality. Based upon the user-supplied information and data characterizing an imaging beam (e.g. a low-Z beam as described above or other imaging beam) the treatment planning system calculates an imaging dose distribution. The treatment planning system receives from the user definition of a target radiation dose distribution and then applies an inverse planning algorithm to generate a treatment plan for delivering a radiation dose distribution that is as close to the target radiation dose distribution as practical. In the inverse planning algorithm the previously-calculated imaging dose is used as a baseline dose.

In some embodiments the incorporation of imaging dose distribution 140 in the dose estimates used in optimizing a radiation treatment plan provides one or more of the following advantages: more accurate estimation of the dose that will be delivered to a subject upon execution of a radiation treatment plan with associated imaging; the opportunity to obtain higher quality images by increasing imaging doses without increasing the overall dose delivered to the subject (since an increase in imaging dose at a location can be compensated for by modifying the treatment plan to decrease the therapeutic dose delivered at that location), and the opportunity to leverage the technology in existing treatment planning systems (treatment planning systems typically include functions for estimating dose distributions and functions for matching beam shapes to target regions, these functions can be modified relatively easily for estimating imaging dose and planning imaging beams).

At imaging machine 122 a subject may be placed in position and imaging instructions 136 may be executed to obtain image data 70. Image data 70 may comprise a VOI CBCT image set, for example. Imaging machine 122 may perform automated co-registration between image data 70 and a target dose distribution. Imaging machine 122 may display alignment indicia indicating where features in image data 70 ought to be located when the subject is properly positioned for treatment. A user may view the images and alignment indicia to determine whether it is necessary to reposition the subject and, if so, to determine repositioning parameters.

In addition or in the alternative, image processing may be performed on image data 70 to locate fiducial features and to compare locations of those fiducial features to target locations. Non-limiting examples of fiducial features are gold seeds that have been implanted in the subject at known locations relative to a target volume; a tumor of a type that can be imaged with sufficient contrast to be detected; features of bones and the like. Radiation delivery machine 122 may include an imaging control that permits the user to view images of a target volume in various planes and/or from various viewpoints to check that surrounding tissues are not receiving more radiation dose than necessary.

Since imaging and therapeutic radiation are both delivered by radiation delivery machine 122 therapy can be done in the course of acquiring an image set or vice versa. This can allow, for example, images to be acquired as therapy proceeds. In some embodiments, images acquired in the course of delivering therapeutic radiation are 2-D images taken in a beam's eye view direction. Such images may be obtained by switching radiation delivery machine 122 into an imaging mode, obtaining an image, and switching radiation delivery machine 122 back into a therapy mode without changing the gantry angle.

In some embodiments a treatment planning system is configured to automatically output instructions for acquiring 2-D images at one or more times during delivery of a fraction. The frequency of imaging may be selectable. Upon execution of the treatment plan the 2-D images may be acquired and displayed on a monitor associated with a radiation delivery machine (e.g. a linear accelerator). An operator viewing the images can verify that the treatment being delivered appears to be delivering the radiation to the desired target volume.

The images may be co-registered with indicia indicating desired alignment of features in the images and/or a representation of the distribution of dose being delivered by the therapeutic radiation (or a combination of the doses from therapeutic radiation and imaging radiation). A user such as a radiation technician or a physician viewing the images can check to ensure that the radiation is being delivered according to plan.

Certain implementations of the invention comprise computer processors which execute software instructions which cause the processors to perform a method of the invention. For example, one or more processors in a treatment planning system or radiation delivery machine may implement the methods of FIGS. 3, 4, 5, 9 and 11 or other methods described above by executing software instructions in a program memory accessible to the processors. The invention may also be provided in the form of a program product. The program product may comprise any medium which carries a set of computer-readable signals comprising instructions which, when executed by a data processor, cause the data processor to execute a method of the invention. Program products according to the invention may be in any of a wide variety of forms. The program product may comprise, for example, physical media such as magnetic data storage media including floppy diskettes, hard disk drives, optical data storage media including CD ROMs, DVDs, electronic data storage media including ROMs, flash RAM, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example:

- The foregoing discussion has described radiation delivery machines of the type in which beam angle is set by rotating a gantry. Other mechanisms may be used to change the beam angle. The term 'gantry angle' is used to describe the angle from which an imaging or therapeutic beam is incident on a subject and does not require a gantry or other specific mechanism be used to set that angle.
- The invention is not limited to applications where therapeutic radiation is delivered in the form of X-rays. Imaging techniques and apparatus according to at least some embodiments may be applied in cases where the therapeutic radiation comprises an electron beam or other particle beam, for example.

Accordingly, the scope of the invention is to be construed in accordance with the substance defined by the following claims.

What is claimed is:

1. A method for planning a radiation treatment for delivery by a radiotherapy apparatus, the method comprising:
   defining at least one set of imaging conditions for imaging with an imaging beam, each set of imaging conditions comprising at least a beam angle and a beam shape for exposing at least one imaging volume of interest to radiation;
   establishing a plan for a therapeutic radiation treatment to be delivered by a treatment beam different from the imaging beam, the plan comprising apertures for a plurality of beam angles;
   estimating a volumetric radiation dose that would result from the at least one set of imaging conditions using first data characterizing the imaging beam;
   estimating a volumetric radiation dose that would result from delivering the plan for a therapeutic radiation treatment using second data characterizing the treatment beam;
   optimizing the apertures to deliver a desired radiation dose to a target region of a subject while maintaining radiation dose to tissues outside of the target region below one or more thresholds while taking into account the estimated volumetric radiation dose for the at least one set of imaging conditions at least in a selected region outside of the target region.

2. A method according to claim 1 wherein optimizing the apertures comprises estimating volumetric radiation doses for the apertures using the second data and summing the volumetric radiation doses for the apertures together with the estimated volumetric radiation dose for the at least one set of imaging conditions.

3. A method according to claim 2 wherein the selected region outside of the target region corresponds to a sensitive tissue desired to be spared by the radiation treatment and the optimization comprises applying a cost function that values minimizing dose to the selected region.

4. A method according to claim 3 comprising counting radiation to be delivered by the at least one set of imaging conditions as a baseline dose contributing to the desired radiation dose to the target region.

5. A method according to claim 1 wherein the imaging beam comprises a radiation beam generated by impinging an electron beam on a first target and the treatment beam comprises a radiation beam generated by impinging the electron beam on a second target.

6. A method according to claim 5 wherein the second target has a higher atomic number than the first target.

7. A method according to claim 6 wherein the first target comprises a low-Z material and the second target comprises a high-Z material.

8. A method according to claim 1 wherein the apertures correspond to a plurality of gantry angles and the imaging conditions correspond to 2D images taken in a beams-eye view direction from one or more of the plurality of gantry angles.

9. A method according to claim 1 wherein the imaging volume of interest is larger than the target region.

10. A method according to claim 1 comprising receiving from a user information specifying a desired imaging quality wherein estimating a volumetric radiation dose that would result from the at least one set of imaging conditions using first data characterizing the imaging beam is based in part on the desired imaging quality.

11. A method according to claim 1 comprising controlling a radiotherapy apparatus to deliver the radiation treatment plan and to acquire an image using the one or more imaging conditions between delivering two of the apertures of the radiation treatment plan.

12. A method according to claim 11 comprising controlling the radiotherapy apparatus to: deliver one or more of the apertures of the radiation treatment plan in a radiation treatment mode; place the radiotherapy machine in an imaging mode; acquire the image; return the radiotherapy apparatus to the radiation treatment mode; and deliver one or more additional ones of the apertures of the radiation treatment plan.

13. A method according to claim 11 wherein the imaging conditions include at least one full-field exposure and at least one exposure wherein acquiring an image comprises shaping a radiation beam to conform with a projection of an imaging volume of interest.

14. A method according to claim 1 comprising defining imaging conditions for a plurality of exposures to image a plurality of imaging volumes of interest wherein the estimated volumetric radiation dose that would result from at least one set of imaging conditions comprises different radiation doses for different ones of the plurality of imaging volumes of interest.

15. A method for planning a radiation treatment, the method comprising:
  planning exposures of a subject to radiation for imaging;
  computing a three-dimensional imaging dose distribution that would result from delivering the imaging exposures;
  planning exposures of the subject to radiation to yield a desired therapeutic radiation dose to a treatment region while using the imaging dose distribution as a baseline dose distribution.

16. A method according to claim 15 wherein planning the exposures of the subject to radiation to yield a desired therapeutic radiation dose comprises applying an inverse planning algorithm.

17. A method according to claim 15 wherein planning the exposures of the subject to radiation for imaging comprises planning exposures to a first radiation beam, planning exposures of the subject to radiation to yield a desired therapeutic radiation dose comprises planning exposures to a second radiation beam, and the first and second radiation beams differ from one another in one or both of energy spectrum and geometry.

18. Apparatus for planning radiation treatments, the apparatus comprising one or more data processors, a program memory accessible to the one or more data processors, the program memory comprising software instructions executable by the one or more processors to configure the one or more processors to:
  plan exposures of a subject to radiation for imaging;
  compute a three-dimensional imaging dose distribution that would result from delivering the imaging exposures; and
  plan exposures of the subject to radiation to yield a desired therapeutic radiation dose to a treatment region while using the imaging dose distribution as a baseline dose distribution.

19. Apparatus according to claim 18 wherein the software instructions comprise instructions providing an inverse planning algorithm and the apparatus is configured to execute the inverse planning algorithm in planning the exposures of the subject to radiation to yield the desired therapeutic radiation dose.

20. Apparatus according to claim 19 wherein the software instructions comprise instructions which calculate a radiation dose to a selected region outside of the treatment region and apply a cost function that values minimizing dose to the selected region.

21. Apparatus according to claim 18 wherein the apparatus comprises stored image beam data characterizing an imaging beam and stored therapy beam data characterizing a therapy beam different from the imaging beam and the apparatus is configured to use the image beam data in determining the imaging dose distribution and to use the therapy beam data in planning the exposures of the subject to radiation to yield the desired therapeutic radiation dose distribution.

22. Apparatus according to claim 21 wherein the imaging beam and the therapy beam differ from one another in one or both of energy spectrum and geometry.

23. Apparatus according to claim 22 wherein the software instructions include instructions for generating beam shaper configurations for shaping the imaging beam to conform with one or more imaging volumes of interest.

24. Apparatus according to claim 22 wherein the apparatus is configured to plan the exposures of a subject to radiation for imaging by determining at least an imaging beam angle and an imaging beam shape for exposing at least one imaging volume of interest to radiation and to plan the exposures of the subject to radiation by determining treatment apertures for a plurality of treatment beam angles.

25. Apparatus according to claim 24 in combination with a radiation source comprising a first target for generating the imaging beam and a second target for generating the therapy beam wherein the apparatus is further configured to deliver control instructions to control the radiation source to: deliver radiation generated using the second target to a subject using the treatment apertures and treatment beam angles and to deliver radiation generated using the first target to a subject using the at least one imaging beam angle and imaging beam shape.

26. Apparatus according to claim 25 wherein the first target comprises a material having an atomic number in the range of 6 to 13.

27. Apparatus according to claim 25 wherein the radiation source comprises a linear accelerator.

28. Apparatus according to claim 27 comprising an imaging radiation detector located to detect the imaging beam after the imaging beam has passed through a subject.

29. Apparatus according to claim 27 comprising an actuator configured to selectably insert the low-Z target or the high-Z target into the path of an electron beam generated by the linear accelerator.

30. An imaging method comprising:
  delivering a radiation treatment to a treatment volume of a subject according to a radiation treatment plan from a plurality of beam angles within a range of angles while shaping the beam to correspond to the treatment volume using a beam shaper;
  for each of a plurality of different beam angles within the range of angles:
    controlling the beam shaper to shape a radiation beam such that delivery of radiation is primarily limited to paths that pass through a plurality of imaging volumes of interest within a subject, the imaging volumes different from the treatment volume;
    obtaining images of radiation that has passed through the imaging volumes of interest; and,
    processing the images to obtain volumetric images of the plurality of imaging volumes of interest.

31. A method according to claim 30 wherein the beam shaper comprises a multileaf collimator and controlling the beam shaper comprises setting positions of leaves of the multileaf collimator.

32. A method according to claim 31 wherein the plurality of volumes of interest comprises at least three distinct volumes of interest.

33. A method according to claim 30 comprising establishing the imaging volumes of interest based on a previously acquired computed tomography image of the subject.

34. A method according to claim 33 wherein the imaging volumes of interest correspond to fiducial areas within the subject.

35. A method according to claim 33 comprising processing the volumetric images of the plurality of volumes of interest to register a current orientation of the subject to a coordinate system.

36. A method according to claim 35 comprising modifying the radiation treatment plan based on the current orientation of the subject.

* * * * *